(12) United States Patent
Connon et al.

(10) Patent No.: US 8,476,441 B2
(45) Date of Patent: Jul. 2, 2013

(54) INTERMEDIATES IN THE ENANTIOSELECTIVE SYNTHESIS OF 3-(AMINOMETHYL)-5-METHYL-HEXANOIC ACID

(75) Inventors: Stephen Joseph Connon, Lucan (IE); Aldo Peschiulli, Lecce (IT); Lyn Markey, Foxrock (IE)

(73) Assignee: The Provost, Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 0 days.

(21) Appl. No.: 13/146,491

(22) PCT Filed: Jan. 29, 2010

(86) PCT No.: PCT/EP2010/051133
§ 371 (c)(1),
(2), (4) Date: Oct. 17, 2011

(87) PCT Pub. No.: WO2010/086429
PCT Pub. Date: Aug. 5, 2010

(65) Prior Publication Data
US 2012/0046468 A1    Feb. 23, 2012

(30) Foreign Application Priority Data

Jan. 29, 2009   (EP) .................................... 09151679

(51) Int. Cl.
*C07C 327/32*   (2006.01)
*C07C 67/12*    (2006.01)
*C07C 227/06*   (2006.01)
*C07D 453/02*   (2006.01)

(52) U.S. Cl.
USPC ............ 546/134; 558/255; 560/190; 562/553

(58) Field of Classification Search
None
See application file for complete search history.

(56) References Cited

U.S. PATENT DOCUMENTS 5,616,793 A    4/1997    Huckabee et al.
7,462,738 B2   12/2008   Hedvati et al.

OTHER PUBLICATIONS

Peschiulli, Aldo et al., "Organocatalytic Asymmetric Addition of Alcohols and Thiols to Activated Electrophiles: Efficient Dynamic Kinetic Resolution and Desymmetrization Protocols", Journal of Organic Chemistry (Jul. 23, 2008), vol. 73, No. 16, pp. 6409-6412.
International Search Report dated Aug. 5, 2010 issued in PCT/EP2010/051133.

*Primary Examiner* — Janet Andres
*Assistant Examiner* — Timothy R Rozof
(74) *Attorney, Agent, or Firm* — Scully, Scott, Murphy & Presser, P.C.

(57) ABSTRACT

(S)-(+)-3-(aminomethyl)-5-methyl-hexanoic acid or (S)-pregabalin is an anticonvulsive drug. In addition to its use as an anticonvulsive agent, pregabalin has also been indicated as a medicament in the treatment of anxiety, neuropathic pain and pain in patients with fibromyalgia. Provided herein are thioester intermediates in the synthesis of and processes for the synthesis of 3-(aminomethyl)-5-methyl-hexanoic acid in the (R) or (S) configuration.

16 Claims, 2 Drawing Sheets

INTERMEDIATES IN THE ENANTIOSELECTIVE SYNTHESIS OF 3-(AMINOMETHYL)-5-METHYL-HEXANOIC ACID

FIELD OF THE INVENTION

The present invention relates to enantioselective methods for the preparation of 3-(aminomethyl)-5-methyl-hexanoic acid and salts and esters thereof. In particular, the present invention provides for a process for the preparation of (S)-(+)-3-(aminomethyl)-5-methyl-hexanoic acid or (S)-pregabalin and salts and esters thereof. The invention further relates to synthetic intermediates of the synthetic processes referred to above.

BACKGROUND TO THE INVENTION (S)-(+)-3-(aminomethyl)-5-methyl-hexanoic acid or (S)-pregabalin (1) is an anticonvulsive drug manufactured and marketed by Pfizer. In its first full year on the market this drug achieved sales in excess of 1 billion US dollars.

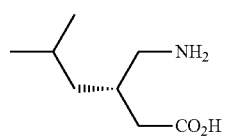

1

In addition to its use as an anticonvulsive agent, pregabalin has also been indicated as a medicament in the treatment of anxiety, neuropathic pain and pain in patients with fibromyalgia.

Two existing syntheses of (S)-(+)-3-(aminomethyl)-5-methyl-hexanoic acid proceed through the meso-anhydride 3-isobutylglutaric anhydride (2).

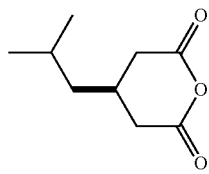

2

U.S. Pat. No. 5,616,793 describes aminolysis of 2 with aqueous ammonia as illustrated in Scheme 1. The resultant racemic amide (A) is resolved by reacting it with (R)-(+)-α-phenylethylamine to yield (R)-(−)-3-(carbamoylmethyl)-5-methyl hexanoic acid, which is in turn subjected to a Hofmann rearrangement to afford (S)-pregabalin. This process suffers in that it is wasteful as the unwanted enantiomer of intermediate A is discarded, and the chiral resolving agent (R)-(+)-α-phenylethylamine has to be employed is substantial quantities and subsequently removed from the reaction.

U.S. Pat. No. 7,462,738 discloses the asymmetric alcoholysis of 3-isobutylglutaric anhydride to afford hemiester B. The overall synthetic strategy is outlined in Scheme 2. Enantioselective alcoholysis of 3-isobutylglutaric anhydride is obtained utilising either a chiral alcohol or an achiral alcohol in combination with a chiral amine. Amidation of enantioenriched hemiester B with aqueous ammonia yields (R)-(−)-3-(carbamoylmethyl)-5-methyl hexanoic acid and a Hofmann rearrangement affords (S)-pregabalin.

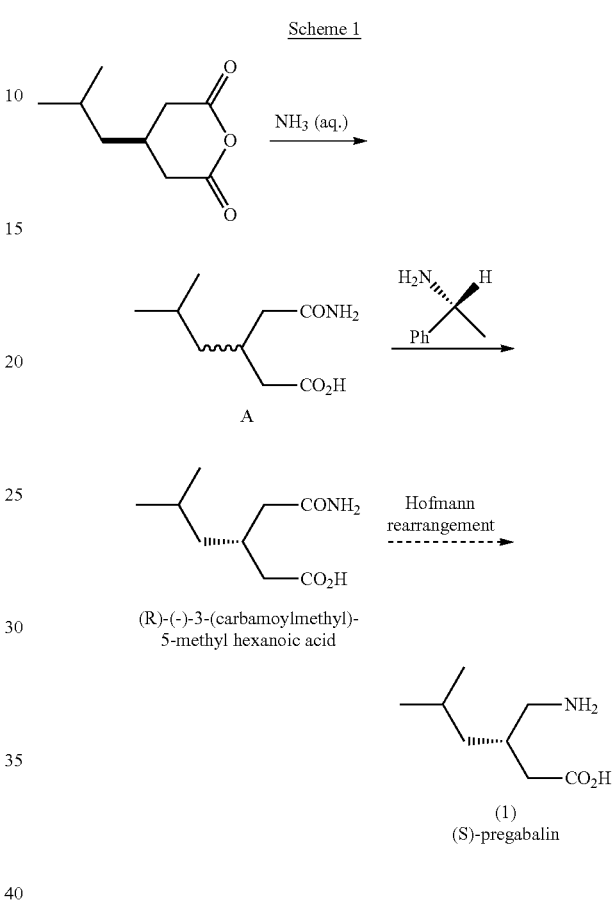

In order to achieve good enantioselectivity, the process of U.S. Pat. No. 7,462,738 necessitates that the chiral alcohol or chiral amine/achiral alcohol combination employed in the alcoholysis step be utilised in an appreciable excess relative to the starting material 3-isobutylglutaric anhydride, i.e. greater than 1:1. In all cases the chiral amine must be employed in stoichiometric amounts. Such an approach is inefficient and costly. Furthermore, exceedingly low temperatures of −50° C. or −78° C. are required for acceptable enantioinduction in the alcoholysis step.

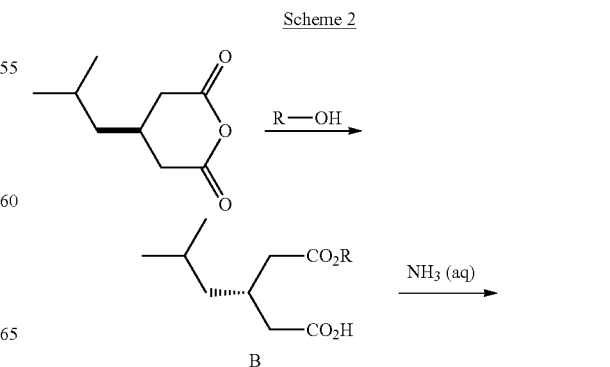

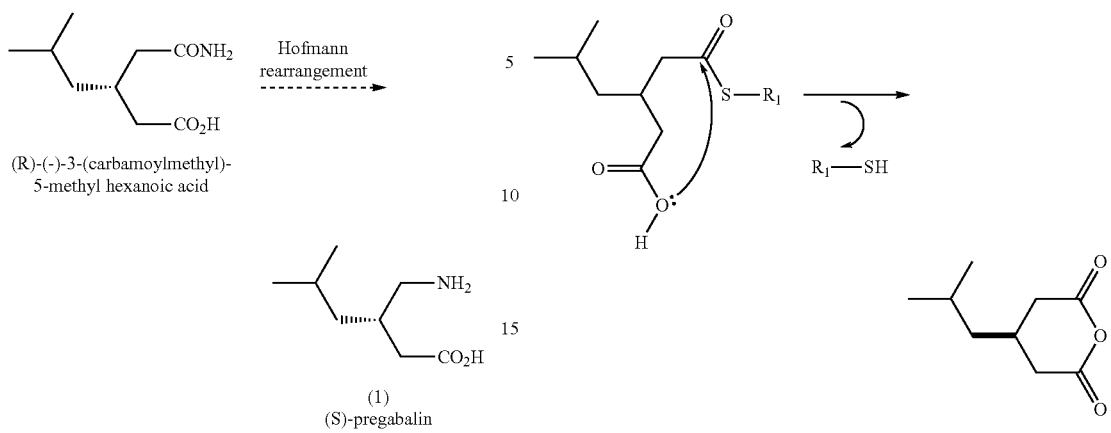

(R)-(−)-3-(carbamoylmethyl)-
5-methyl hexanoic acid (1)
(S)-pregabalin

Notwithstanding the state of the art it would still be desirable to provide alternative enantioselective synthetic methods for preparing 3-(aminomethyl)-5-methyl-hexanoic acid. Ideally, such methods would provide for high enantioselectivity at ambient temperature and enantioinduction would be achievable utilising a chiral catalyst in sub-stoichiometric quantities relative to the starting reagent, thereby affording an efficient and economic synthetic process.

SUMMARY OF THE INVENTION

The present invention provides for a thiol-based synthetic intermediate in the enantioselective synthesis of 3-(aminomethyl)-5-methyl-hexanoic acid. The invention further provides for a process for the enantioselective preparation of 3-(aminomethyl)-5-methyl-hexanoic acid utilising such intermediates. The present invention also affords an enantioselective synthesis of 3-(aminomethyl)-5-methyl-hexanoic acid via alcoholysis of 3-isobutylglutaric anhydride utilising a chiral catalyst.

In one aspect, the present invention provides for a compound of the general formula (I), or a salt, or ester thereof,

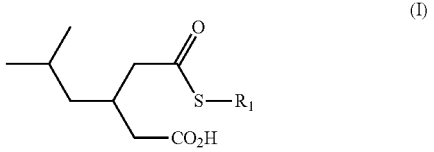

(I)

wherein $R_1$ is chosen such that elimination of a thiol ($R_1$—SH) to generate 3-isobutylglutaric anhydride is thermodynamically disfavoured. $R_1$ may be chosen such that the $pK_a$ ($H_2O$) of $R_1$—SH is greater than 4. $R_1$ may be chosen such that the $pK_a$ ($H_2O$) of $R_1$—SH is greater than 6. $R_1$ may be chosen such that the $pK_a$ ($H_2O$) of $R_1$—SH is greater than 8.

The mechanism by which a thiol could be eliminated to generate 3-isobutylglutaric anhydride is detailed in Scheme 3 (infra). Accordingly, $R_1$ is chosen such that the reaction shown is Scheme 3 does not proceed, i.e. the thioester product is thermodynamically more stable than separate thiol and 3-isobutylglutaric anhydride products.

Scheme 3

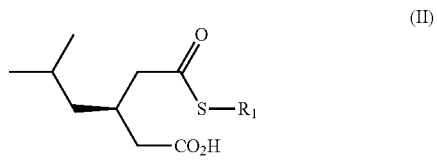

$R_1$ may be selected from the group consisting of $C_1$-$C_{15}$ alkyl, $C_3$-$C_{15}$ cycloalkyl, $C_5$-$C_{15}$ aromatic and combinations thereof. $R_1$ may be selected from $C_1$-$C_{15}$ alkyl, $C_3$-$C_{15}$ cycloalkyl or combinations thereof. As used herein, the term "$C_x$-$C_y$ alkyl" embraces $C_x$-$C_y$ unbranched alkyl, $C_x$-$C_y$ branched alkyl and combinations thereof. $R_1$ as defined above may comprise a primary or secondary carbon atom directly bonded to S. Desirably, $R_1$ does not comprise a tertiary carbon atom directly bonded to S. $R_1$ may be selected from ethyl, propyl, butyl, 3-propenyl, benzyl, 2-propyl, 4-tertbutyl benzyl, cyclopentyl, cyclohexyl, or phenyl. $R_1$ may be ethyl, propyl, butyl, 3-propenyl, benzyl, 2-propyl, 4-tertbutyl benzyl, cyclopentyl, or cyclohexyl.

The compound (I) may find use as an intermediate in the synthesis of 3-(aminomethyl)-5-methyl-hexanoic acid.

The compound of the present invention may be of the general formula (II), or a salt, or ester thereof, (II)

wherein $R_1$ is chosen such that elimination of a thiol ($R_1$—SH) to generate 3-isobutylglutaric anhydride is thermodynamically disfavoured. $R_1$ may be chosen such that the $pK_a$ ($H_2O$) of $R_1$—SH is greater than 4. $R_1$ may be chosen such that the $pK_a$ ($H_2O$) of $R_1$—SH is greater than 6. $R_1$ may be chosen such that the $pK_a$ ($H_2O$) of $R_1$—SH is greater than 8.

$R_1$ may be selected from the group consisting of $C_1$-$C_{15}$ alkyl, $C_3$-$C_{15}$ cycloalkyl, $C_5$-$C_{15}$ aromatic and combinations thereof. $R_1$ may be selected from $C_1$-$C_{15}$ alkyl, $C_3$-$C_{15}$ cycloalkyl and combinations thereof. $R_1$ as defined above may comprise a primary or secondary carbon atom directly bonded to S. Desirably, $R_1$ does not comprise a tertiary carbon atom directly bonded to S. $R_1$ may be selected from ethyl, propyl, butyl, 3-propenyl, benzyl, 2-propyl, 4-tertbutyl benzyl, cyclopentyl, cyclohexyl, or phenyl. $R_1$ may be ethyl, propyl, butyl, 3-propenyl, benzyl, 2-propyl, 4-tertbutyl benzyl, cyclopentyl, or cyclohexyl.

In the embodiment within formula (II), the absolute configuration of the chiral centre of the compound of the present invention is (R). Compound (II) may find utility as an intermediate in the enantioselective synthesis of (R)-3-(aminomethyl)-5-methyl-hexanoic acid.

Alternatively, the compound of the present invention may be of the general formula (III), or a salt, or ester thereof,

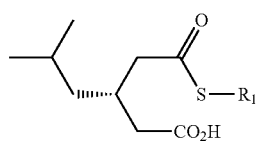

(III)

wherein $R_1$ is chosen such that elimination of a thiol ($R_1$—SH) to generate 3-isobutylglutaric anhydride is thermodynamically disfavoured. $R_1$ may be chosen such that the $pK_a$ ($H_2O$) of $R_1$—SH is greater than 4. $R_1$ may be chosen such that the $pK_a$ ($H_2O$) of $R_1$—SH is greater than 6. $R_1$ may be chosen such that the $pK_a$ ($H_2O$) of $R_1$—SH is greater than 8.

$R_1$ may be selected from the group consisting of $C_1$-$C_{15}$ alkyl, $C_3$-$C_{15}$ cycloalkyl, $C_5$-$C_{15}$ aromatic and combinations thereof. $R_1$ may be selected from $C_1$-$C_{15}$ alkyl, $C_3$-$C_{15}$ cycloalkyl and combinations thereof. $R_1$ as defined above may comprise a primary or secondary carbon atom directly bonded to S. Desirably, $R_1$ does not comprise a tertiary carbon atom directly bonded to S. $R_1$ may be selected from ethyl, propyl, butyl, 3-propenyl, benzyl, 2-propyl, 4-tertbutyl benzyl, cyclopentyl, cyclohexyl, or phenyl. $R_1$ may be ethyl, propyl, butyl, 3-propenyl, benzyl, 2-propyl, 4-tertbutyl benzyl, cyclopentyl, or cyclohexyl.

In the embodiment within formula (III), the absolute configuration of the chiral centre of the compound of the present invention is (S). Compound (III) may find utility as an intermediate in the enantioselective synthesis of (S)-3-(aminomethyl)-5-methyl-hexanoic acid.

Within the context of this specification, the term "enantioselective" refers to a synthetic process that produces one enantiomer of a product in preference to the other enantiomer.

The present invention further provides for a process for the preparation of a compound according to the present invention, or a salt, or ester thereof comprising thiolysis of 3-isobutylglutaric anhydride. Thiolysis of 3-isobutylglutaric anhydride will result in a thioester compound according to the present invention. For example, a compound of the general formula (I).

Desirably, the present invention provides for a process for the enantioselective preparation of a compound according to the present invention, or a salt, or ester thereof comprising enantioselective thiolysis of 3-isobutylglutaric anhydride. Advantageously, such an enantioselective process will produce one enantiomer of a compound according to the present invention in preference to the other. For example, a compound of the general formula (II) in preference to a compound of the general formula (III) and vice versa.

As used herein, thiolysis of 3-isobutylglutaric anhydride comprises ring opening of the cyclic anhydride with a thiol, to yield a compound having a thioester functional group.

The enantioselective thiolysis step may comprise ring opening 3-isobutylglutaric anhydride using a chiral thiol. Suitable chiral thiols may be selected from the group consisting of (R)-1-phenylethanethiol, (S)-1-phenylethanethiol, (R)-1-(1)-naphtylethanethiol, (S)-1-(1)-naphtylethanethiol, (1S,2R)-2-phenylcyclohexanethiol, (1R,2S)-2-phenylcyclohexanethiol, N-Boc-L-cysteine methyl ester, and N-Boc-D-cysteine methyl ester. Such a list is representative only and is by no means limiting on the scope of the invention.

Alternatively, the enantioselective thiolysis step may comprise ring opening 3-isobutylglutaric anhydride using an achiral thiol and a chiral catalyst.

The achiral thiol is chosen such that upon thiolysis of 3-isobutylglutaric anhydride, it is thermodynamically disfavoured for the thioester compound to eliminate a thiol ($R_1$—SH) to re-generate 3-isobutylglutaric anhydride. The achiral thiol may be chosen such that the $pK_a$ ($H_2O$) of $R_1$—SH is greater than 4. The achiral thiol may be chosen such that the $pK_a$ ($H_2O$) of $R_1$—SH is greater than 6. The achiral thiol may be chosen such that the $pK_a$ ($H_2O$) of $R_1$—SH is greater than 8.

The achiral thiol may be selected from the group consisting of $C_1$-$C_{15}$ alkane thiols, $C_3$-$C_{15}$ cycloalkyl thiols, $C_5$-$C_{15}$ aromatic thiols and combinations thereof. The achiral thiol may be selected from $C_1$-$C_{15}$ alkyl, $C_3$-$C_{15}$ cycloalkyl and combinations thereof. The achiral thiol may comprise a primary or secondary thiol. Desirably, the achiral thiol does not comprise a tertiary thiol. The achiral thiol may be selected from the group comprising ethane thiol, propane thiol, butane thiol, propene-3-thiol, benzylmercaptan, 2-propane thiol, 4-tertbutylbenzyl mercaptan, cyclopentane thiol, cyclohexane thiol, and thiophenol.

The term "catalyst" refers to a molecule in the reaction mixture that enhances the rate of reaction and is used in sub-stoichiometric loading relative to the reactants. The term "chiral catalyst" refers to a chiral molecule in the reaction mixture, used in substoichiometric loading relative to the 3-isobutylglutaric anhydride. The chiral catalyst imparts a chiral influence on the reaction between the thiol and 3-isobutylglutaric anhydride to afford the chiral thioester product in high enantioselectivity.

The (chiral) catalyst loading with respect to 3-isobutylglutaric anhydride may be 0.1-50 mol %, for example 0.1-25 mol %, such as 0.1-10 mol %. Desirably, the catalyst loading with respect to 3-isobutylglutaric anhydride is 0.5-2 mol %. This represents a highly economic and efficient catalyst loading.

In one embodiment, the chiral catalyst comprises:

i) a Lewis acid functional group to enhance the electrophilicity of 3-isobutylglutaric anhydride; and ii) a Lewis base functional group to enhance the nucleophilicity of the achiral thiol.

By enhancing the nucleophilicity of a first reaction component and enhancing the electrophilicity of a second reaction component the catalyst greatly enhances the rate of reaction between both components. As will be appreciated by a person skilled in the art, such catalysts are often termed bifunctional catalysts as they can activate the 3-isobutylglutaric anhydride electrophile and the achiral thiol nucleophile simultaneously, thereby facilitating reaction of both components in a chiral environment.

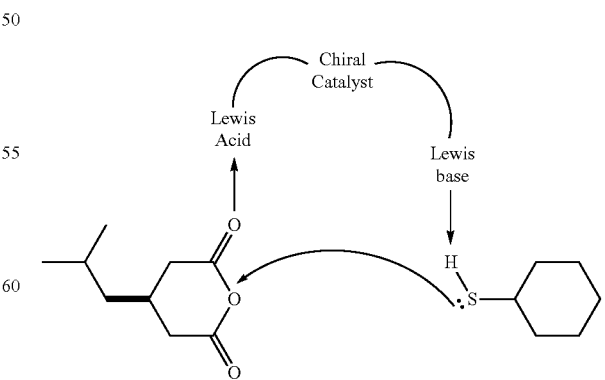

The chiral catalyst may be selected from the group consisting of:

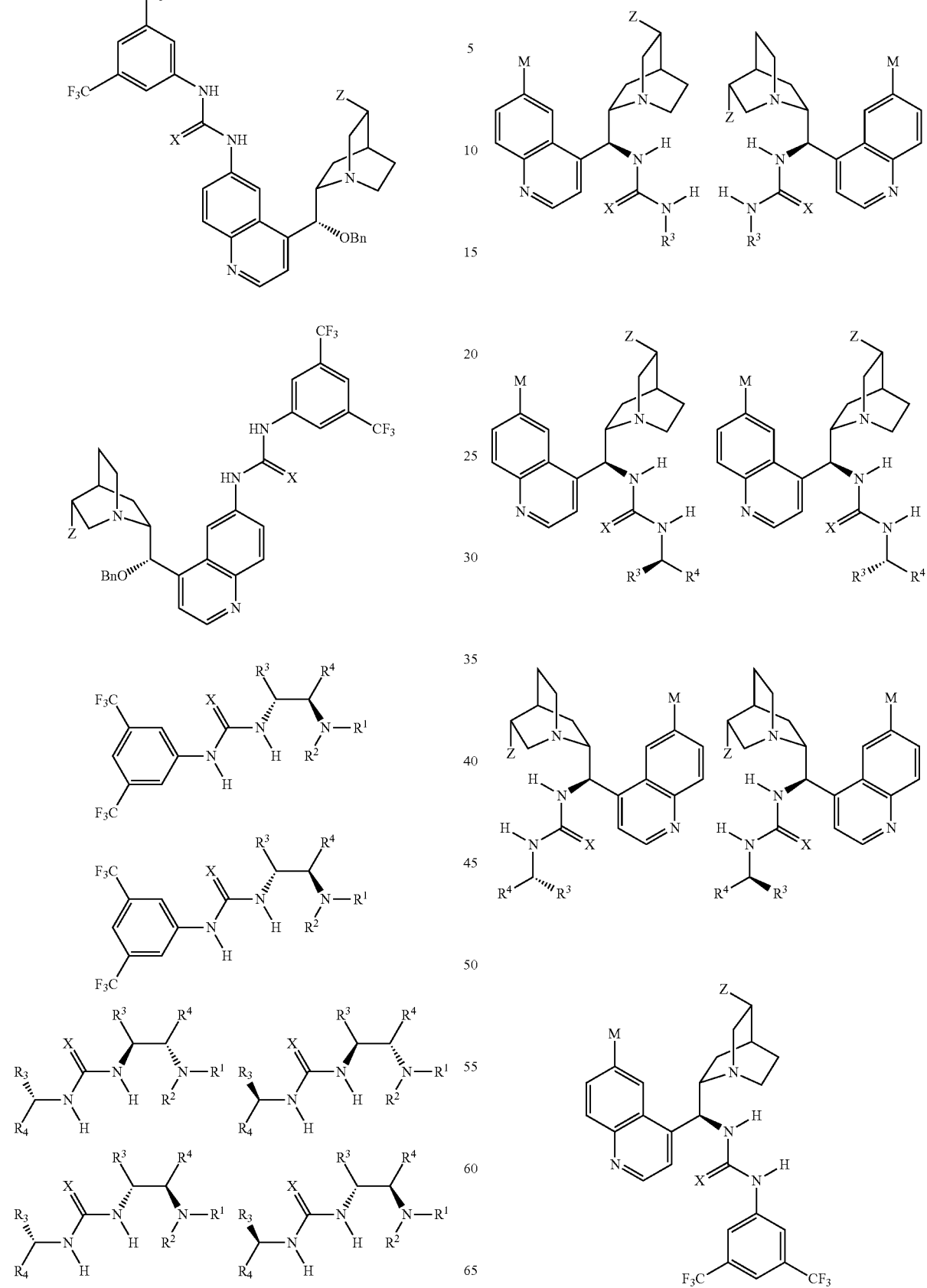

-continued

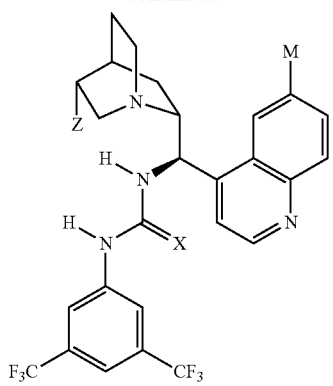

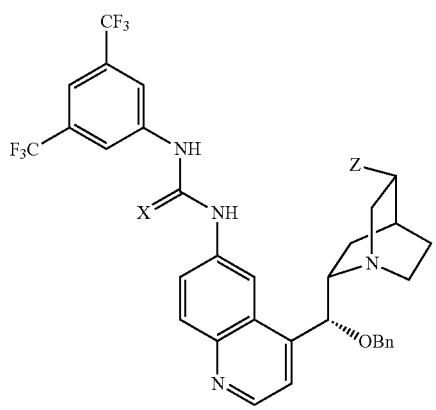

wherein X can be O or S;

Z can be a single or double bond;

M can be H, OH, or OMe;

$R_1$ and $R_2$ can be the same or different and may comprise $C_1$-$C_{15}$ alkyl (optionally substituted with halogens or cycloalkyl groups), or $R_1$ and $R_2$ may together define a $C_3$-$C_{15}$ cycloalkyl alkyl ring; and $R_3$ and $R_4$ can be the same or different and may comprise $C_1$-$C_{15}$ alkyl (optionally substituted with halogens or cycloalkyl groups), or $R_3$ and $R_4$ may together define a $C_3$-$C_{15}$ cycloalkyl alkyl ring or $C_5$-$C_{15}$ aromatic ring.

As used herein, the statement "Z can be a single or double bond" indicates that the substituent Z can be a single or double bond (i.e. not an element of the periodic table) and embraces the following non-limiting examples:

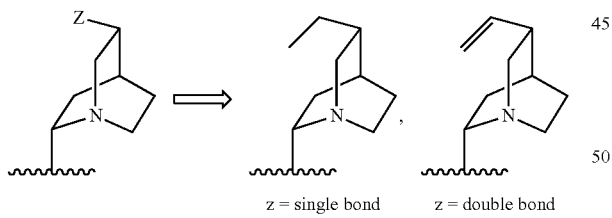

z = single bond    z = double bond

As used herein, the statement "$R_1$ and $R_2$ may together define a $C_3$-$C_{15}$ cycloalkyl alkyl ring" indicates that $R_1$ and $R_2$ may form an alkyl ring structure of which the N atom is an integral component of the ring structure, i.e. $R_1$—N—$R_2$ define a heterocyclic alkyl ring. For the avoidance of any doubt, the shorthand "Bn" takes its conventional meaning of "benzyl" in this specification.

The chiral catalyst may be selected from the group consisting of:

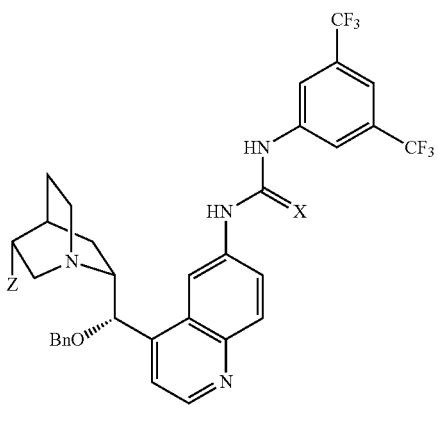

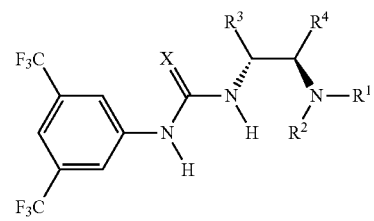

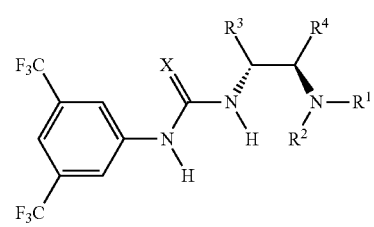

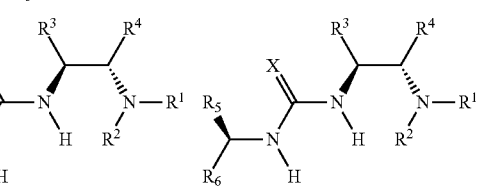

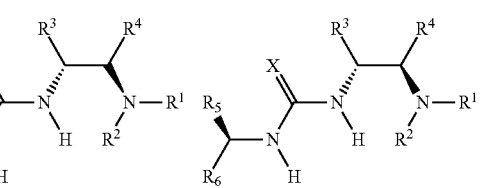

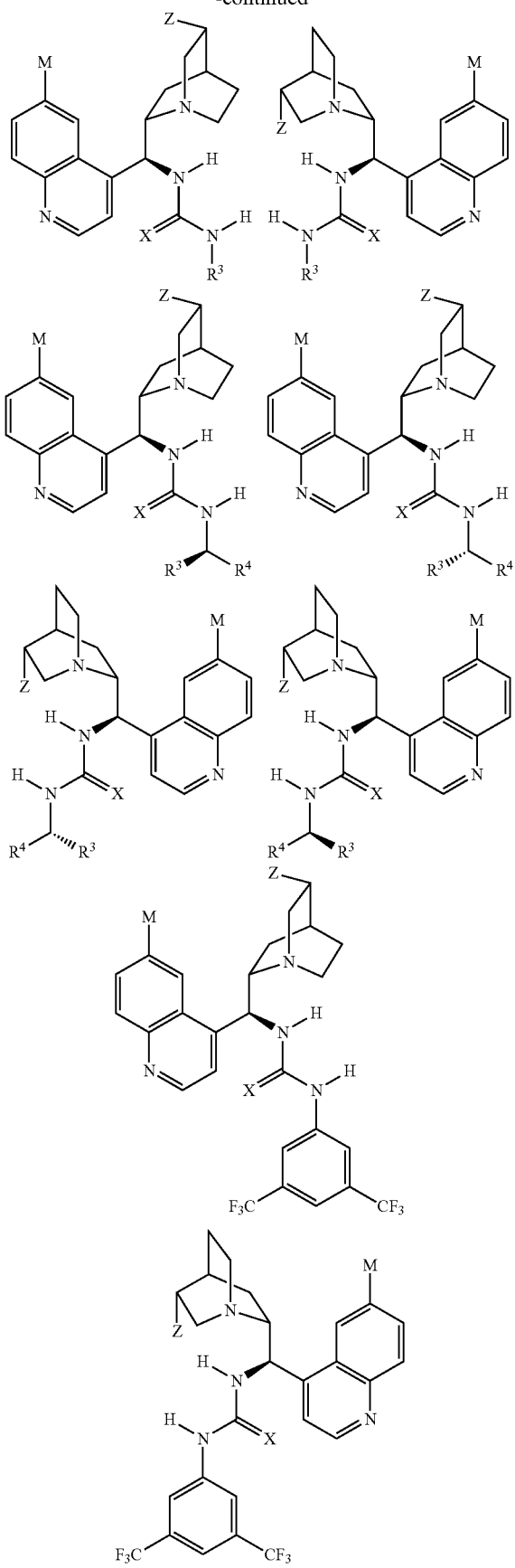

wherein X can be O or S;

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

$R_1$ and $R_2$ can be the same or different and may comprise $C_1$-$C_{15}$ alkyl, or $R_1$ and $R_2$ may together define a $C_3$-$C_{15}$ cycloalkyl ring, wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_3$ and $R_4$ can be the same or different and may comprise $C_1$-$C_{15}$ alkyl, or $R_3$ and $R_4$ may together define a $C_3$-$C_{15}$ cycloalkyl ring or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_5$ and $R_6$ can be the same or different and may comprise $C_1$-$C_{15}$ alkyl, or $R_5$ and $R_6$ may together define a $C_3$-$C_{15}$ cycloalkyl ring, or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

The chiral catalyst may be selected from the group comprising

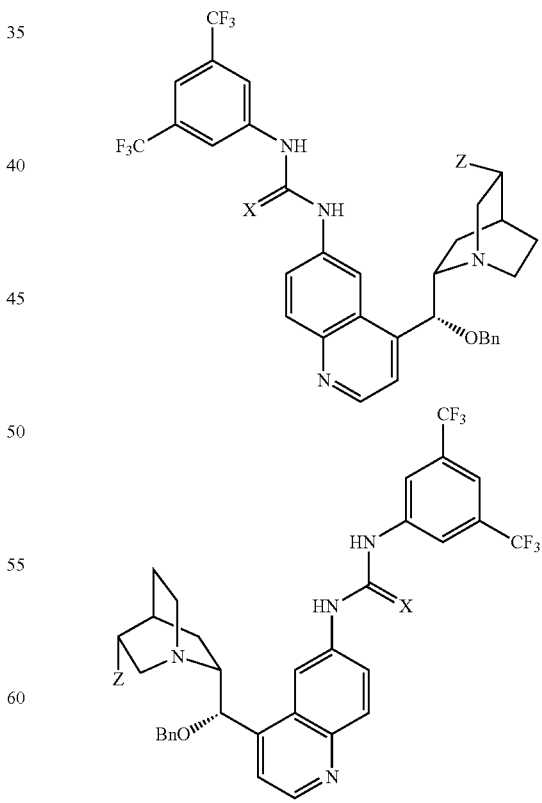

wherein X can be O or S; and
Z can be a single or double bond.

Alternatively, the chiral catalyst may be selected from the group comprising

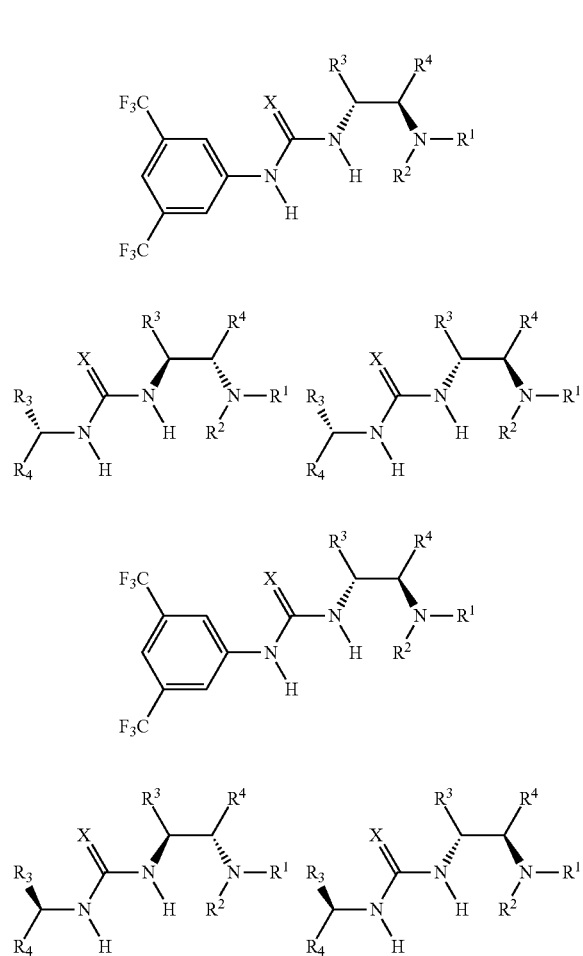

wherein X can be O or S;

$R_1$ and $R_2$ can be the same or different and may comprise $C_1$-$C_{15}$ alkyl, or $R_1$ and $R_2$ may together define a $C_3$-$C_{15}$ cycloalkyl alkyl ring; and $R_3$ and $R_4$ can be the same or different and may comprise $C_1$-$C_{15}$ alkyl, or $R_3$ and $R_4$ may together define a $C_3$-$C_{15}$ cycloalkyl alkyl ring or $C_5$-$C_{15}$ aromatic ring.

In yet a further alternative embodiment, the chiral catalyst may be selected from

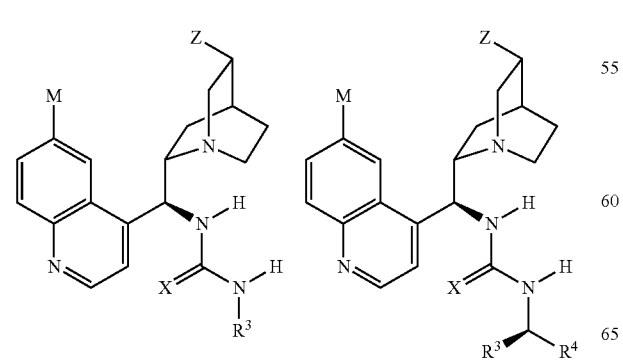

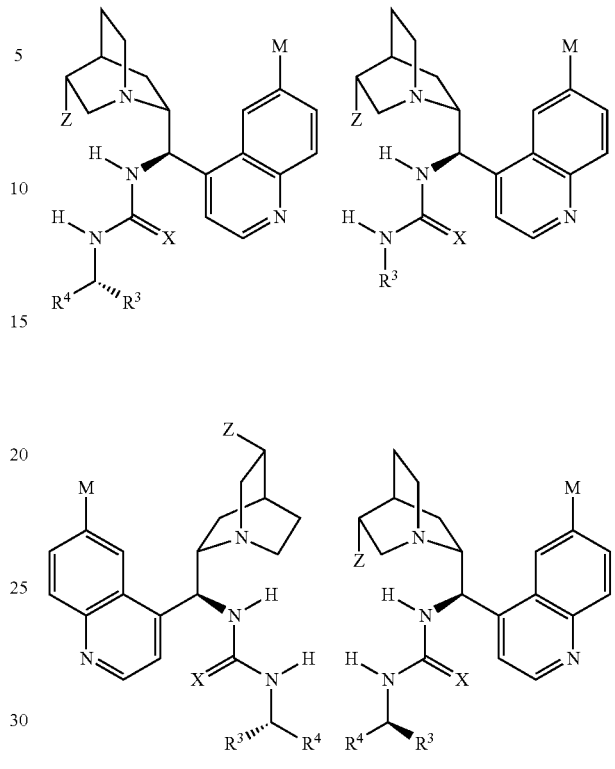

wherein X can be O or S;

Z can be a single or double bond;

M can be H, OH, or OMe; and $R_3$ and $R_4$ can be the same or different and may comprise $C_1$-$C_{15}$ alkyl, or $R_3$ and $R_4$ may together define a $C_3$-$C_{15}$ cycloalkyl alkyl ring or $C_5$-$C_{15}$ aromatic ring.

The chiral catalyst may be selected from the group comprising:

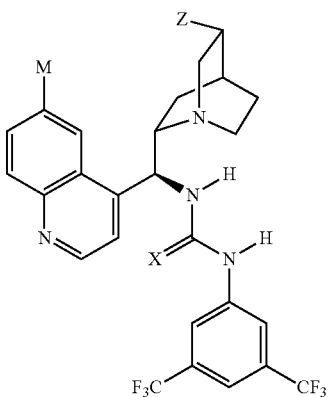

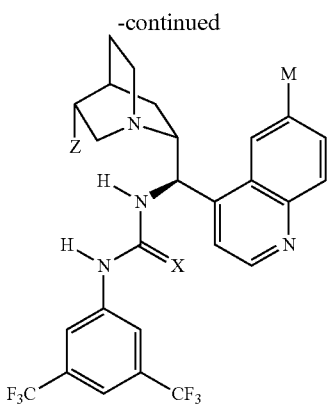

wherein X can be O or S;
Z can be a single or double bond; and
M can be H, OH, or OMe.
Desirably, the chiral catalyst is selected from the group comprising:

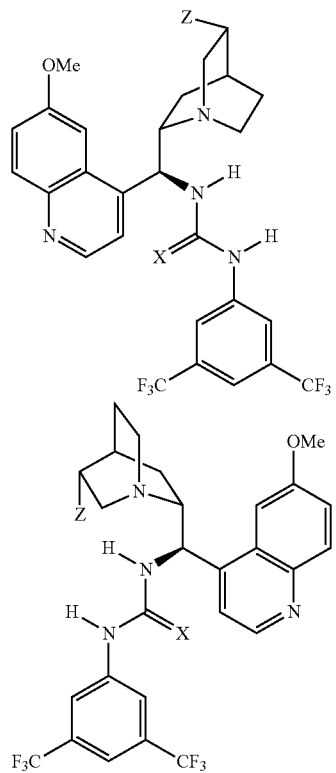

wherein Z can be a double or single bond.

In one embodiment Z is a double bond. These catalysts are readily prepared from commercially available starting materials quinine or quinidine and conduct enantioselective thiolysis of 3-isobutylglutaric anhydride with excellent yield and enantioselectivity.

Enantioselective thiolysis of 3-isobutylglutaric anhydride using an achiral thiol and a chiral catalyst affords the compound of the present invention in excellent yield and enantioselectivity at room temperature.

The process of the present invention may be carried out in a solvent selected from the group consisting of $C_5$-$C_{12}$ hydrocarbons, $C_6$-$C_{12}$ aromatic hydrocarbons, $C_3$-$C_{12}$ ketones (cyclic and acyclic), $C_2$-$C_{12}$ ethers (cyclic and acyclic), $C_2$ to $C_{12}$ esters, $C_2$-$C_5$ nitriles and combinations thereof. Desirably, the solvent is ethereal. For example, $C_2$-$C_{12}$ ethers (cyclic and acyclic). Suitable ethers may be selected from the group consisting of diethylether, THF, 2-methyl THF, diisopropylether, methyltertbutylether (MTBE) and combinations thereof. In a preferred embodiment, the solvent is methyltertbutylether (MTBE).

In a further aspect the present invention provides for a process for the enantioselective preparation of a compound of the general formula (IV) or (V), or a salt thereof, comprising:

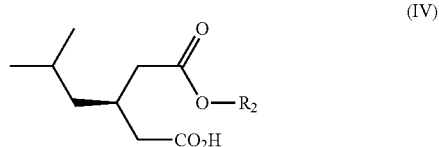

(IV)

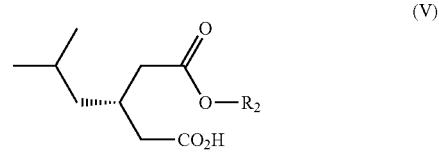

(V)

enantioselective alcoholysis of 3-isobutylglutaric anhydride to afford a compound having an ester functional group, wherein enantioselective alcoholysis of 3-isobutylglutaric anhydride comprises ring opening 3-isobutylglutaric anhydride using an achiral alcohol and a chiral catalyst selected from the group consisting of:

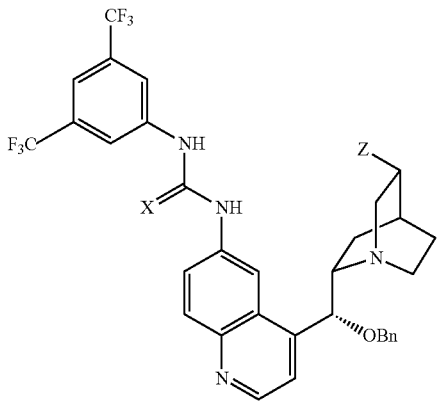

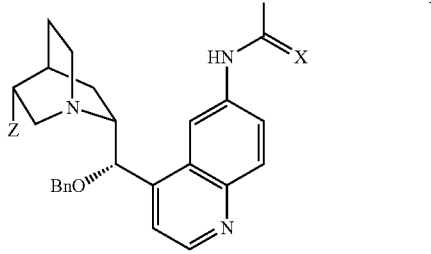

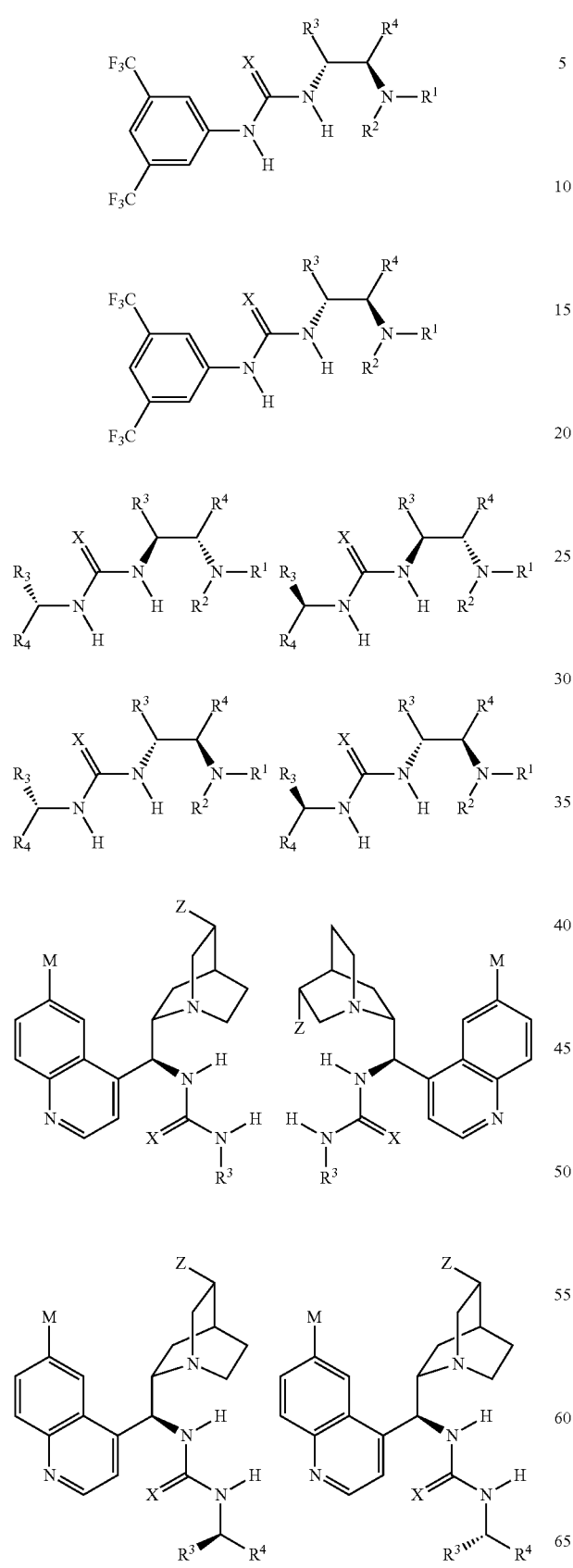

wherein X can be O or S;

Z can be a single or double bond;

M can be H, OH, or OMe;

$R_1$ and $R_2$ can be the same or different and may comprise $C_1$-$C_{15}$ alkyl (optionally substituted with halogens or cycloalkyl groups), or $R_1$ and $R_2$ may together define a $C_3$-$C_{15}$ cycloalkyl alkyl ring; and $R_3$ and $R_4$ can be the same or different and may comprise $C_1$-$C_{15}$ alkyl (optionally substituted with halogens or cycloalkyl groups), or $R_3$ and $R_4$ may together define a $C_3$-$C_{15}$ cycloalkyl alkyl ring or $C_5$-$C_{15}$ aromatic ring.

The chiral catalyst may be selected from the group consisting of:

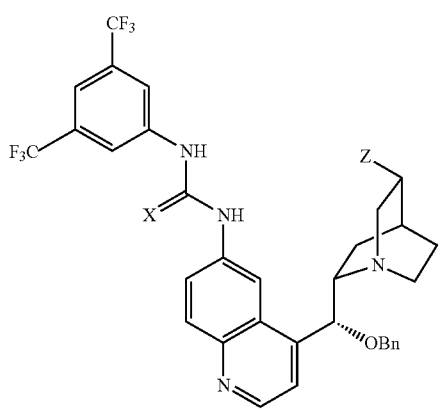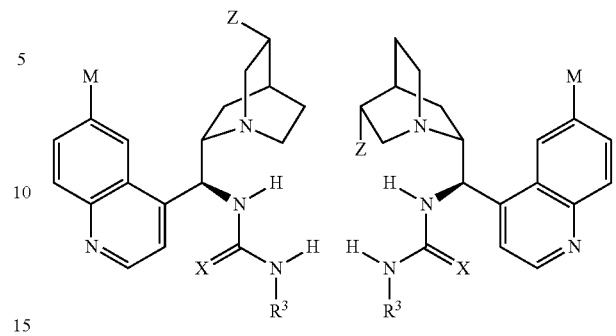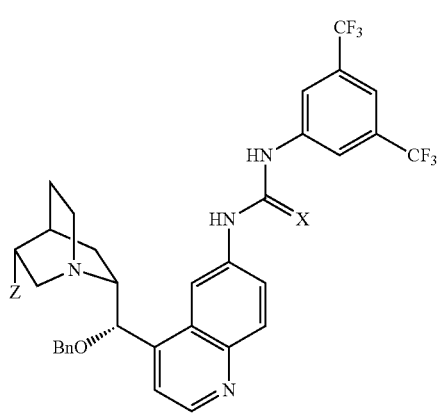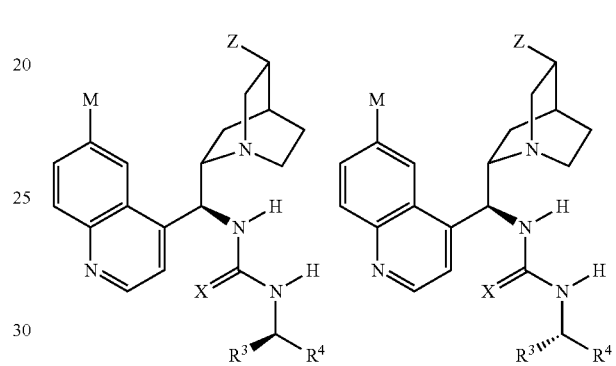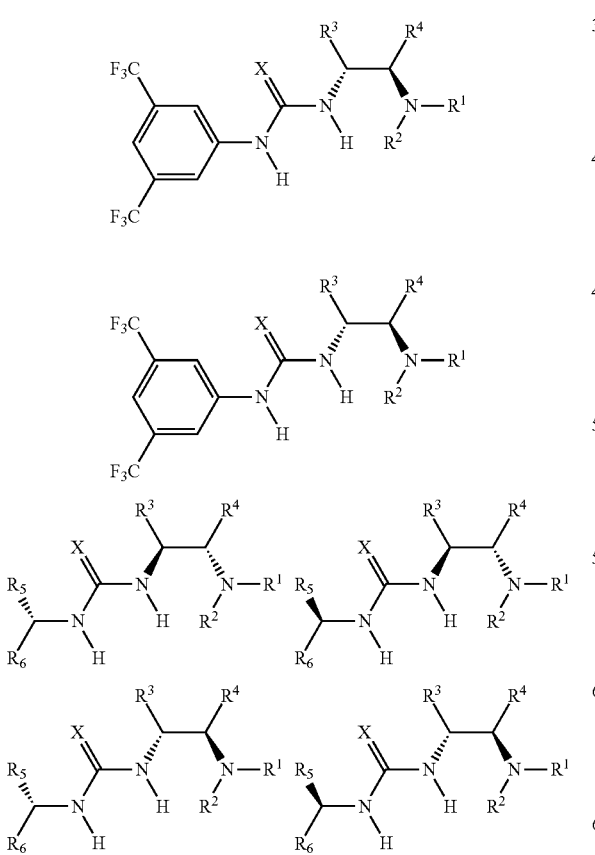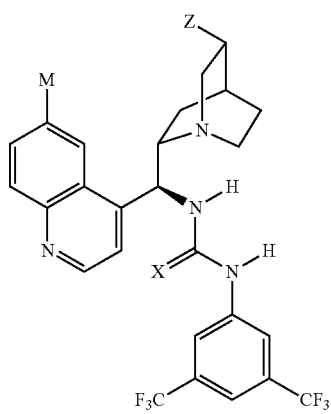

-continued

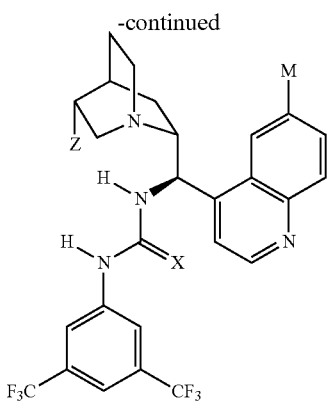

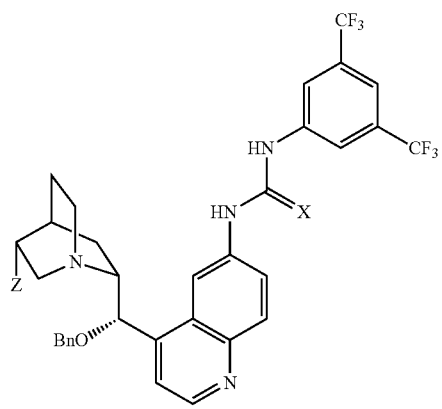

wherein X can be O or S;

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

$R_1$ and $R_2$ can be the same or different and may comprise $C_1$-$C_{15}$ alkyl, or $R_1$ and $R_2$ may together define a $C_3$-$C_{15}$ cycloalkyl ring, wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_3$ and $R_4$ can be the same or different and may comprise $C_1$-$C_{15}$ alkyl, or $R_3$ and $R_4$ may together define a $C_3$-$C_{15}$ cycloalkyl ring or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_5$ and $R_6$ can be the same or different and may comprise $C_1$-$C_{15}$ alkyl, or $R_5$ and $R_6$ may together define a $C_3$-$C_{15}$ cycloalkyl ring, or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

The chiral catalyst may be selected from the group comprising

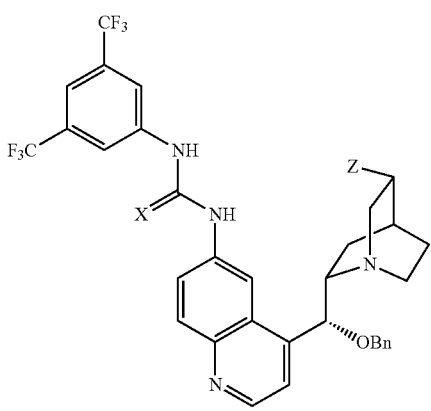

wherein X can be O or S; and

Z can be a single or double bond.

Alternatively, the chiral catalyst may be selected from the group comprising

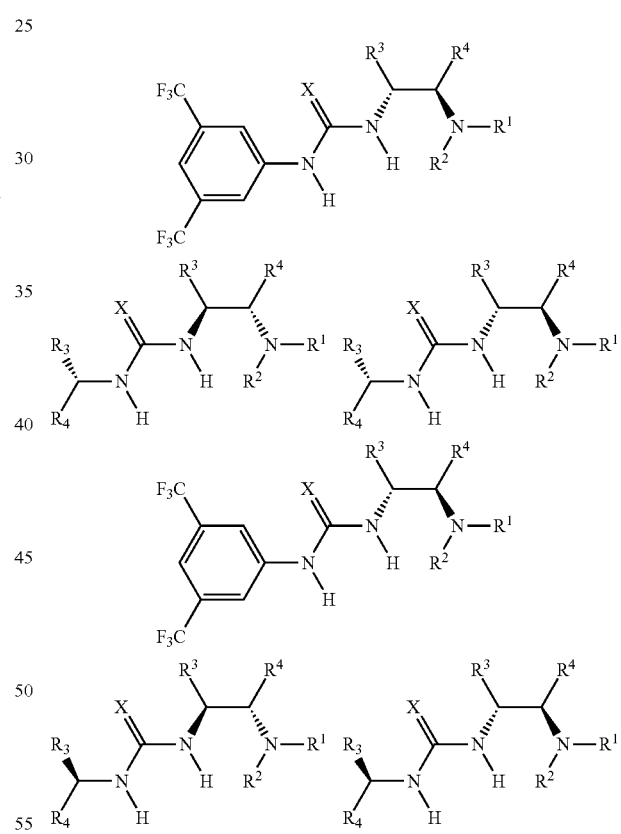

wherein X can be O or S;

$R_1$ and $R_2$ can be the same or different and may comprise $C_1$-$C_{15}$ alkyl, or $R_1$ and $R_2$ may together define a $C_3$-$C_{15}$ cycloalkyl alkyl ring; and $R_3$ and $R_4$ can be the same or different and may comprise $C_1$-$C_{15}$ alkyl, or $R_3$ and $R_4$ may together define a $C_3$-$C_{15}$ cycloalkyl alkyl ring or $C_5$-$C_{15}$ aromatic ring.

In yet a further alternative embodiment, the chiral catalyst may be selected from the group of:

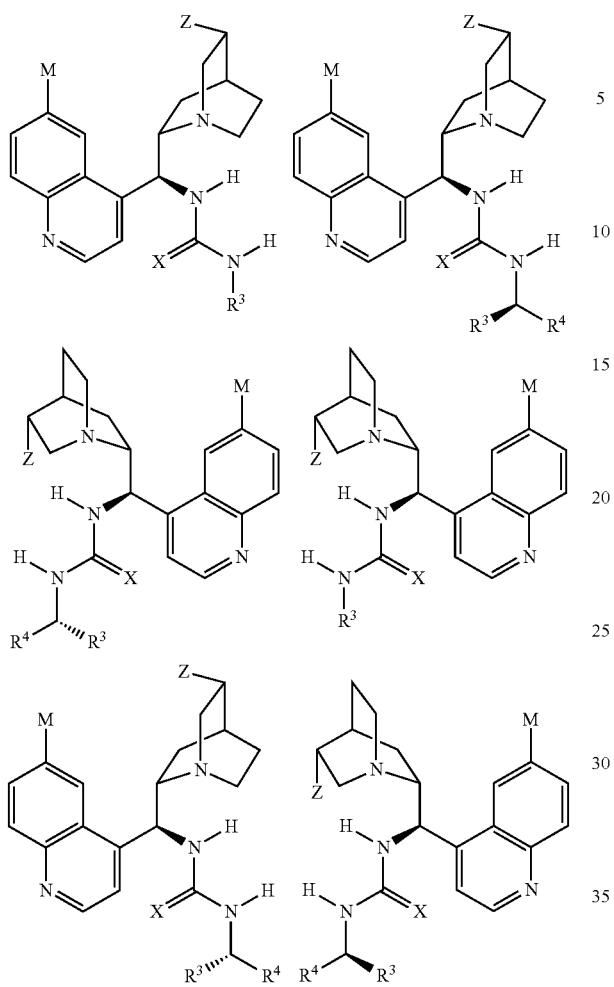

wherein X can be O or S;
Z can be a single or double bond;
M can be H, OH, or OMe; and
$R_3$ and $R_4$ can be the same or different and may comprise $C_1$-$C_{15}$ alkyl, or $R_3$ and $R_4$ may together define a $C_3$-$C_{15}$ cycloalkyl alkyl ring or $C_5$-$C_{15}$ aromatic ring.

The chiral catalyst may be selected from the group comprising:

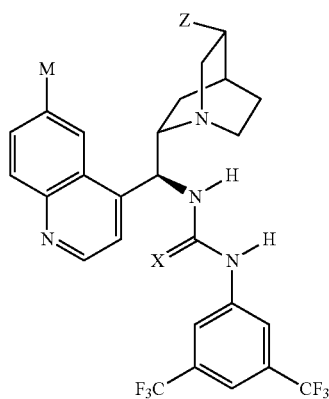

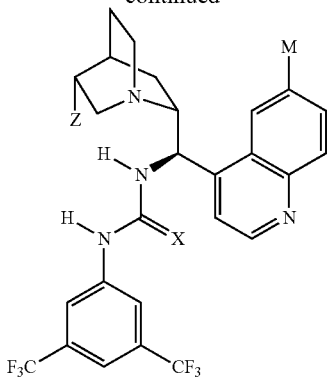

wherein X can be O or S;
Z can be a single or double bond; and
M can be H, OH, or OMe.

Desirably, the chiral catalyst is selected from the group comprising:

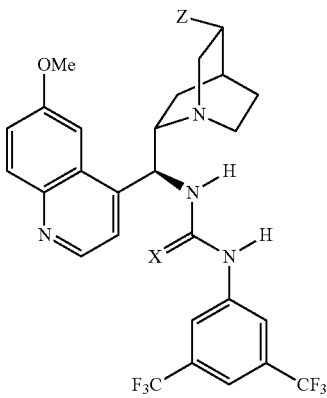

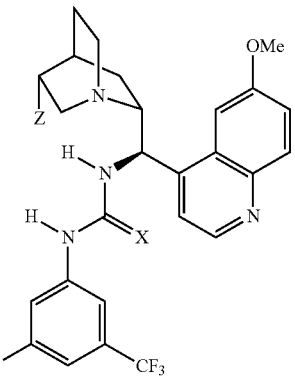

wherein Z can be a double or single bond.

In one embodiment Z is a double bond.

Advantageously, the enantioselective alcoholysis process of the present invention for producing products (IV) or (V) is the first example of a catalytic process with low catalyst loadings with respect to 3-isobutylglutaric anhydride. For example, the catalyst loading may be 0.1-50 mol %, for example 0.1-25 mol %, such as 0.1-10 mol %. Desirably, the catalyst loading with respect to 3-isobutylglutaric anhydride is 0.5-2 mol %. This represents a highly economic and efficient catalyst loading.

In addition, the enantioselective alcoholysis process of the present invention is the first example of an ambient temperature process capable of affording products (IV) or (V) in high enantioselectivity.

The achiral alcohol may be selected from the group consisting of $C_1$-$C_{15}$ alkyl alcohols, $C_3$-$C_{15}$ cycloalkyl alcohols, $C_5$-$C_{15}$ aromatic alcohols and combinations thereof. The achiral alcohol may be selected from the group consisting of $C_1$-$C_{15}$ alkyl alcohols, $C_3$-$C_{15}$ cycloalkyl alcohols and combinations thereof. Suitably, the achiral alcohol may be a $C_1$-$C_{10}$ alkyl alcohol. For example, the achiral alcohol may be one of methanol, ethanol, propanol, benzyl alcohol or allyl alcohol.

The product of the enantioselective alcholysis having an ester functional group may be of the general formula (IV), or a salt thereof,

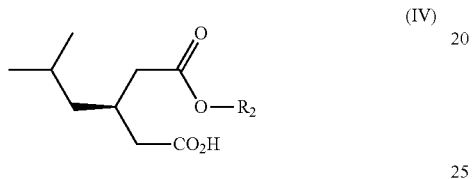
(IV)

wherein $R_2$ is selected from the group consisting of $C_1$-$C_{15}$ alkyl, $C_3$-$C_{15}$ cycloalkyl, $C_5$-$C_{15}$ aromatic and combinations thereof. $R_2$ may be selected from the group consisting of $C_1$-$C_{15}$ alkyl alcohols, $C_3$-$C_{15}$ cycloalkyl alcohols and combinations thereof.

The product of the enantioselective alcoholysis having an ester functional group may be of the general formula (V), or a salt thereof,

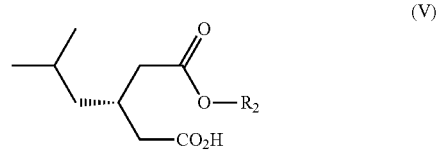
(V)

wherein $R_2$ is selected from the group consisting of $C_1$-$C_{15}$ alkyl, $C_3$-$C_{15}$ cycloalkyl, $C_5$-$C_{15}$ aromatic and combinations thereof. $R_2$ may be selected from the group consisting of $C_1$-$C_{15}$ alkyl alcohols, $C_3$-$C_{15}$ cycloalkyl alcohols and combinations thereof.

The above process may be carried out in a solvent selected from the group consisting of $C_5$-$C_8$ hydrocarbons, $C_6$-$C_{10}$ aromatic hydrocarbons, $C_3$-$C_{10}$ ketones (cyclic and acyclic), $C_2$-$C_{10}$ ethers (cyclic and acyclic), $C_2$ to $C_{10}$ esters, $C_2$-$C_5$ nitriles and combinations thereof. Desirably, the solvent is ethereal. For example, $C_2$-$C_{12}$ ethers (cyclic and acyclic). Suitable ethers may be selected from the group consisting of diethylether, THF, 2-methyl THF, diisopropylether, methyl-tertbutylether (MTBE) and combinations thereof. In a preferred embodiment, the solvent is methyltertbutylether (MTBE). In a preferred embodiment, the solvent is methyl-tertbutylether (MTBE).

The present invention further provides for a process for the preparation of 3-(aminomethyl)-5-methyl-hexanoic acid comprising:
 i) thiolysis of 3-isobutylglutaric anhydride according to the process of the present invention to afford an intermediate having a thioester functional group; and
 ii) converting the thioester functional group into an amine.

In a further aspect, the present invention affords a process for the enantioselective preparation of 3-(aminomethyl)-5-methyl-hexanoic acid comprising:
 i) enantioselective thiolysis of 3-isobutylglutaric anhydride according to the process of the present invention to afford a chiral intermediate having a thioester functional group; or
 ii) enantioselective alcoholysis of 3-isobutylglutaric anhydride according to the process of the present invention to afford a chiral intermediate having an ester functional group; and
 iii) converting the thioester or ester functional group into an amine.

The chiral intermediate having a thioester functional group may be of the general formula (II) or (III), or a salt, or ester thereof,

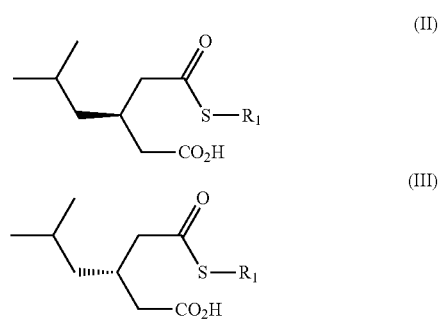

wherein $R_1$ is chosen such that elimination of a thiol ($R_1$—SH) to generate 3-isobutylglutaric anhydride is thermodynamically disfavoured. $R_1$ may be chosen such that the $pK_a$ ($H_2O$) of $R_1$—SH is greater than 4. $R_1$ may be chosen such that the $pK_a$ ($H_2O$) of $R_1$—SH is greater than 6. $R_1$ may be chosen such that the $pK_a$ ($H_2O$) of $R_1$—SH is greater than 8.

$R_1$ may be selected from the group consisting of $C_1$-$C_{15}$ alkyl, $C_3$-$C_{15}$ cycloalkyl, $C_5$-$C_{15}$ aromatic and combinations thereof. $R_1$ may be selected from $C_1$-$C_{15}$ alkyl, $C_3$-$C_{15}$ cycloalkyl and combinations thereof. $R_1$ as defined above may comprise a primary or secondary carbon atom directly bonded to S. Desirably, $R_1$ does not comprise a tertiary carbon atom directly bonded to S. $R_1$ may be selected from ethyl, propyl, butyl, 3-propenyl, benzyl, 2-propyl, 4-tertbutyl benzyl, cyclopentyl, cyclohexyl, or phenyl. $R_1$ may be ethyl, propyl, butyl, 3-propenyl, benzyl, 2-propyl, 4-tertbutyl benzyl, cyclopentyl, or cyclohexyl.

In the embodiment within formula (II) the 3-(aminomethyl)-5-methyl-hexanoic acid produced is (R)-3-(aminomethyl)-5-methyl-hexanoic acid. In the embodiment within formula (III) the 3-(aminomethyl)-5-methyl-hexanoic acid produced is (S)-3-(aminomethyl)-5-methyl-hexanoic acid.

The chiral intermediate having an ester functional group may be of the general formula (IV) or (V), or a salt thereof,

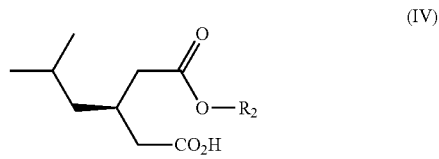
(IV)

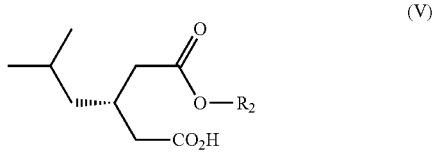

wherein $R_2$ is selected from the group consisting of $C_1$-$C_{15}$ alkyl, $C_3$-$C_{15}$ cycloalkyl, $C_5$-$C_{15}$ aromatic and combinations thereof. $R_2$ may be selected from the group consisting of $C_1$-$C_{15}$ alkyl alcohols, $C_3$-$C_{15}$ cycloalkyl alcohols and combinations thereof.

In the embodiment within formula (IV) the 3-(aminomethyl)-5-methyl-hexanoic acid produced is (R)-3-(aminomethyl)-5-methyl-hexanoic acid. In the embodiment within formula (V) the 3-(aminomethyl)-5-methyl-hexanoic acid produced is (S)-3-(aminomethyl)-5-methyl-hexanoic acid.

The step of converting the thioester or ester functional group into an amine may comprise:
  i) aminolysis of the thioester or ester functional group to yield an amide; and
  ii) subjecting the amide product of step i) to a Hofmann rearrangement.

Aminolysis of the thioester or ester functional group comprises treating the thioester with ammonia or an amine. Preferably, aminolysis of the thioester or ester functional group comprises treating the thioester or ester with ammonia to yield a primary amide. The Hofmann rearrangement is an eminent synthetic transformation which converts an amide to an amine with the loss of carbon monoxide. All protocols for effecting this transformation are embraced by the present invention.

As will be appreciated by a person skilled in the art, the thiol utilised in the enantioselective thiolysis of 3-isobutylglutaric anhydride will be chosen such that aminolysis of the thioester intermediate does not result in racemisation of the product, as per Scheme 4 (infra). The thiol may be chosen such that the $pK_a$ ($H_2O$) of $R_1$—SH is greater than 4. The thiol may be chosen such that the $pK_a$ ($H_2O$) of $R_1$—SH is greater than 6. The thiol may be chosen such that the $pK_a$ ($H_2O$) of $R_1$—SH is greater than 8.

In particular, highly acidic thiols would be unsuitable in this regard as the resultant thioester is likely to be unstable, and ring closure to re-generate 3-isobutylglutaric anhydride could result in racemisation of the product.

Advantageously, the intermediate having a thioester functional group produced by the process of the present invention undergoes aminolysis more rapidly and under milder conditions that the corresponding ester intermediates.

Unlike prior art processes for the enantioselective preparation of 3-(aminomethyl)-5-methyl-hexanoic acid, the process of the present invention allows for the synthesis of either enantiomer of 3-(aminomethyl)-5-methyl-hexanoic acid in excellent yield and enantiomeric excess at ambient temperature or just below. In addition, the inventive process of the present invention allows for very low catalyst loadings with no decrease in yield. Furthermore, the process of the present invention is highly efficient as it does not produce 50% of the unwanted enantiomer. These advantages combine to make the process of the present invention very economic and amenable to industrial scale up.

The skilled person will appreciate that the process for the preparation of compounds of the present invention can also be carried out at temperatures of 0° C. or below.

In a further aspect, the present invention provides for use of a chiral catalyst in sub-stoichiometric loading relative to the reactants in a process for the enantioselective synthesis of 3-(aminomethyl)-5-methyl-hexanoic acid.

The invention further provides for use of a chiral catalyst for
  i) enantioselective thiolysis of 3-isobutylglutaric anhydride; or
  ii) enantioselective alcoholysis of 3-isobutylglutaric anhydride,
wherein the catalyst is in sub-stoichiometric loading relative to 3-isobutylglutaric anhydride,
in a process for the enantioselective synthesis of 3-(aminomethyl)-5-methyl-hexanoic acid.

In one embodiment the chiral catalyst comprises:
  i) a Lewis acid functional group to enhance the electrophilicity of an electrophile; and
  ii) a Lewis base functional group to enhance the nucleophilicity of a nucleophile.

Suitable catalysts may be selected from the group consisting of:

Scheme 4

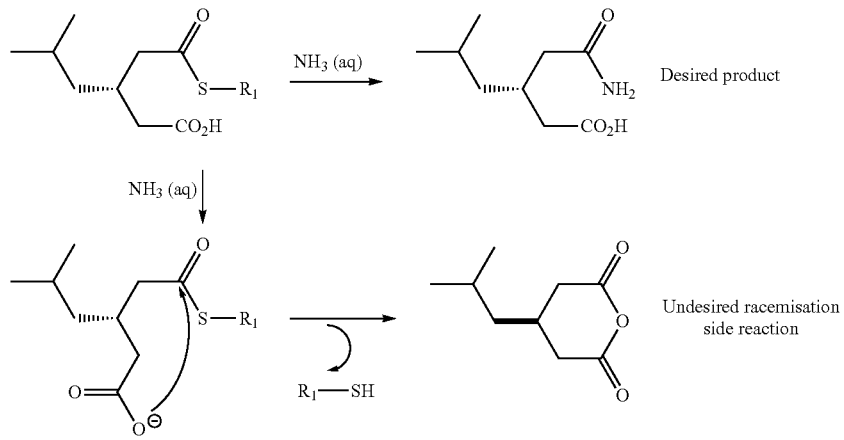

Desired product

Undesired racemisation side reaction

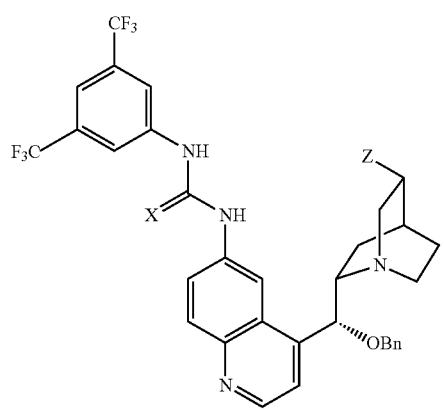
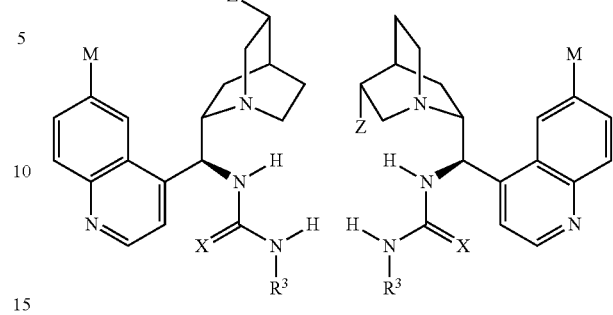
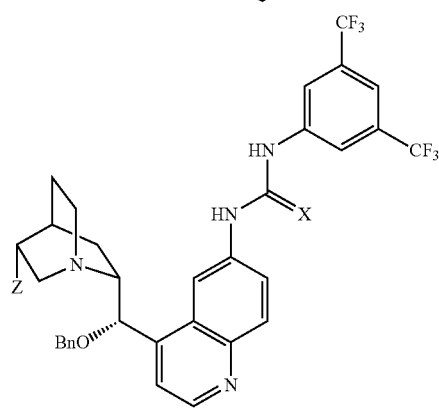
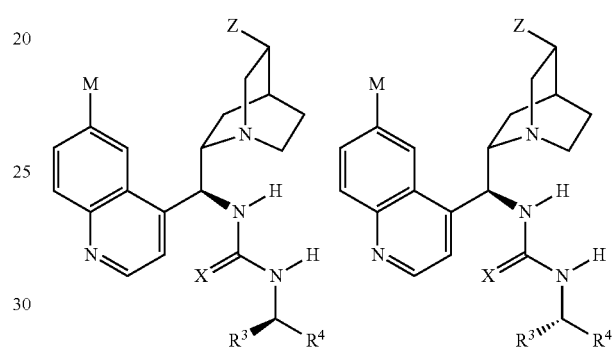
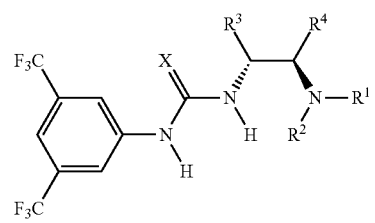
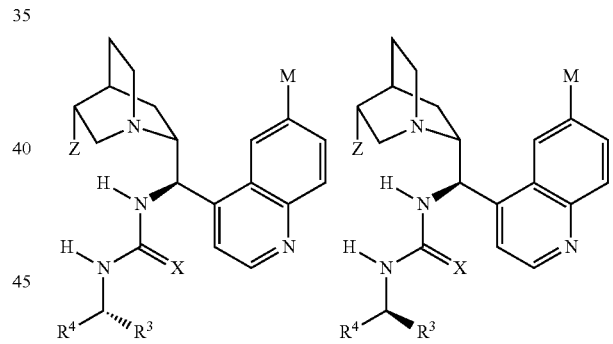
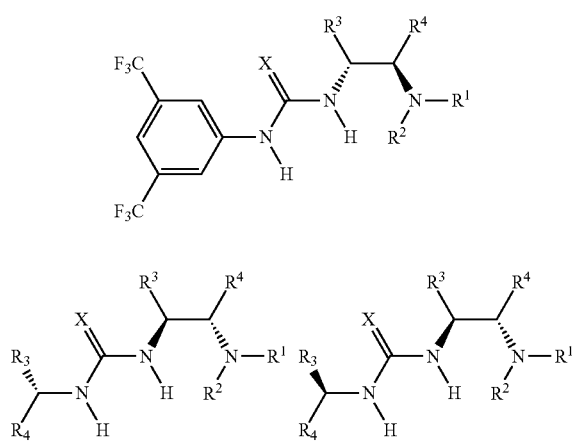
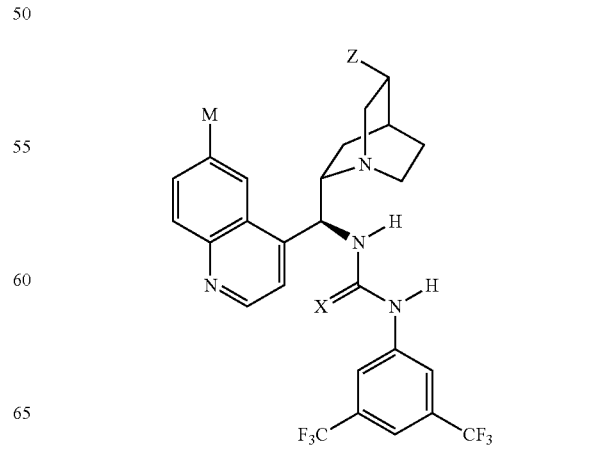

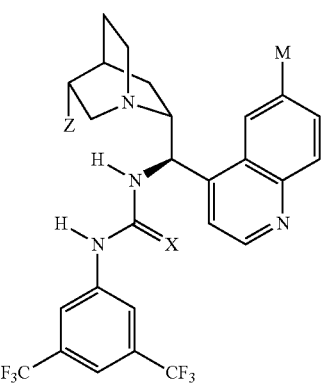

wherein X can be O or S;

Z can be a single or double bond;

M can be H, OH, or OMe;

$R_1$ and $R_2$ can be the same or different and may comprise $C_1$-$C_{15}$ alkyl (optionally substituted with halogens or cycloalkyl groups), or $R_1$ and $R_2$ may together define a $C_3$-$C_{15}$ cycloalkyl alkyl ring; and $R_3$ and $R_4$ can be the same or different and may comprise $C_1$-$C_{15}$ alkyl (optionally substituted with halogens or cycloalkyl groups), or $R_3$ and $R_4$ may together define a $C_3$-$C_{15}$ cycloalkyl alkyl ring or $C_5$-$C_{15}$ aromatic ring.

The chiral catalyst may be selected from the group consisting of:

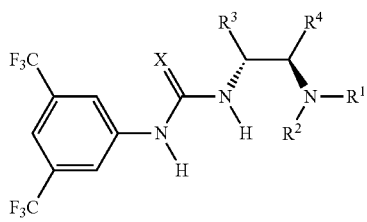

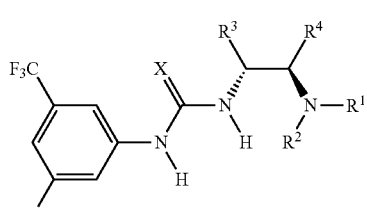

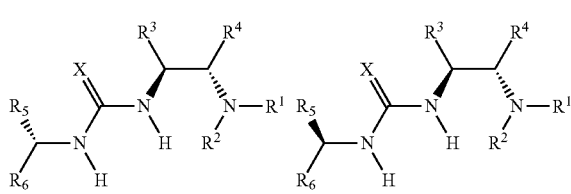

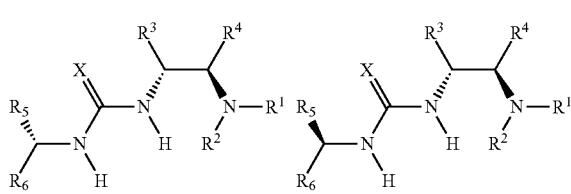

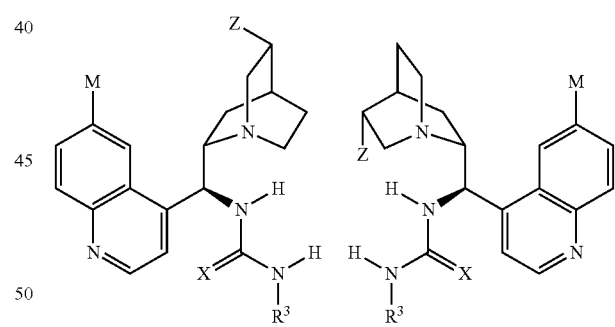

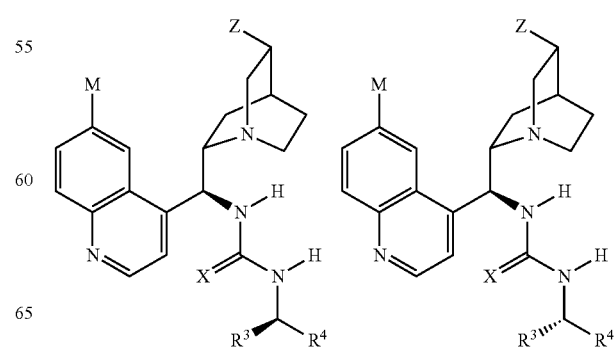

-continued

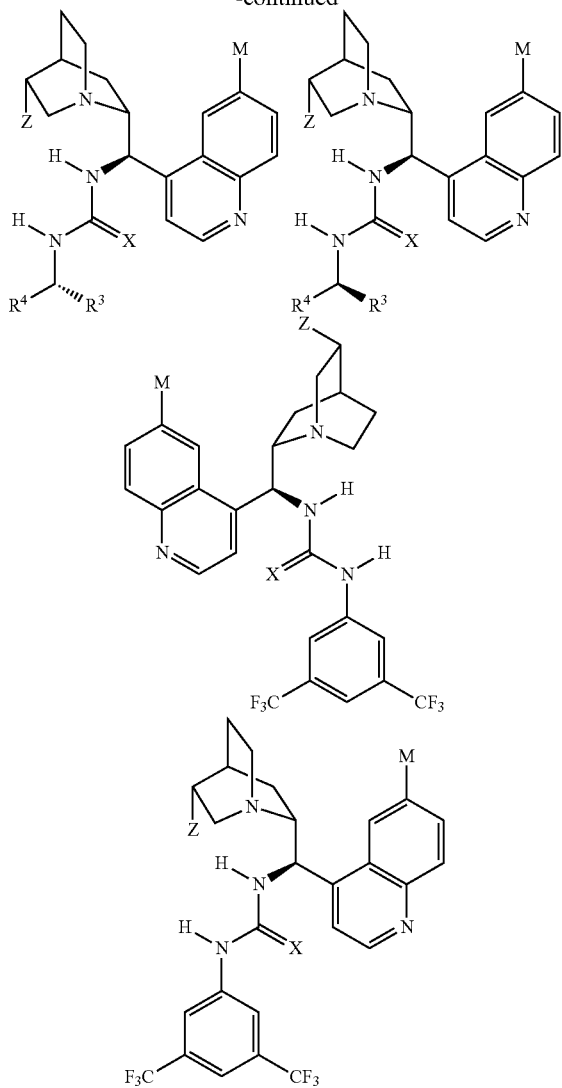

wherein X can be O or S;
Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;
M can be H, OH, or OMe;
$R_1$ and $R_2$ can be the same or different and may comprise $C_1$-$C_{15}$ alkyl, or $R_1$ and $R_2$ may together define a $C_3$-$C_{15}$ cycloalkyl ring, wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and
$R_3$ and $R_4$ can be the same or different and may comprise $C_1$-$C_{15}$ alkyl, or $R_3$ and $R_4$ may together define a $C_3$-$C_{15}$ cycloalkyl ring or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and
$R_5$ and $R_6$ can be the same or different and may comprise $C_1$-$C_{15}$ alkyl, or $R_5$ and $R_6$ may together define a $C_3$-$C_{15}$ cycloalkyl ring, or a $C_5$-$C_{15}$ aryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

The electrophile may be 3-isobutylglutaric anhydride. The nucleophile may be a thiol or an alcohol.

The chiral catalyst may be selected from the group comprising

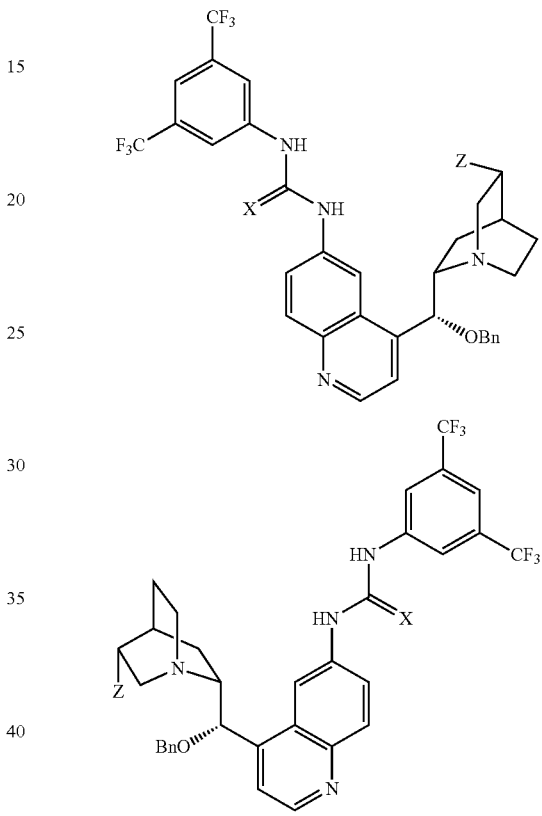

wherein X can be O or S; and
Z can be a single or double bond.

Alternatively, the chiral catalyst may be selected from the group comprising

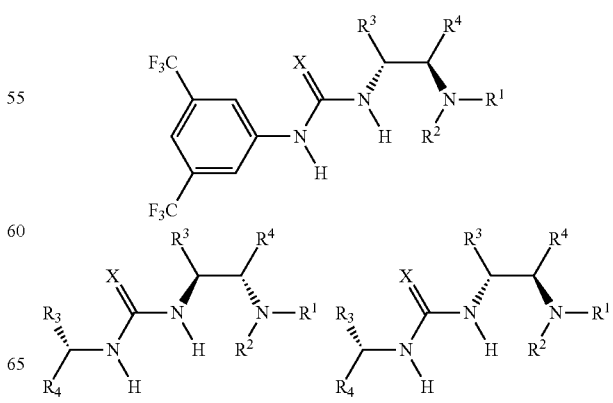

-continued

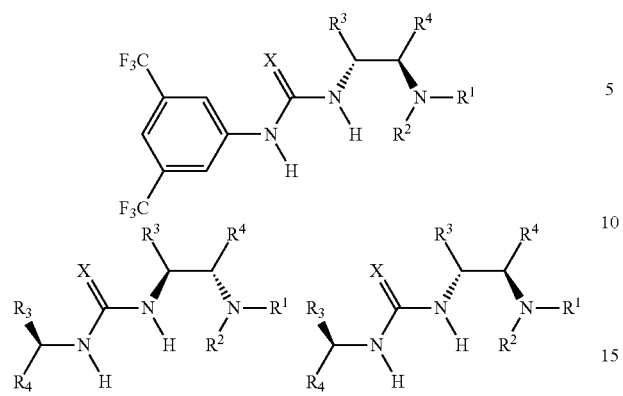

wherein X can be O or S;

R$_1$ and R$_2$ can be the same or different and may comprise C$_1$-C$_{15}$ alkyl, or R$_1$ and R$_2$ may together define a C$_3$-C$_{15}$ cycloalkyl alkyl ring; and R$_3$ and R$_4$ can be the same or different and may comprise C$_1$-C$_{15}$ alkyl, or R$_3$ and R$_4$ may together define a C$_3$-C$_{15}$ cycloalkyl alkyl ring or C$_5$-C$_{15}$ aromatic ring.

In yet a further alternative, the chiral catalyst may be selected from

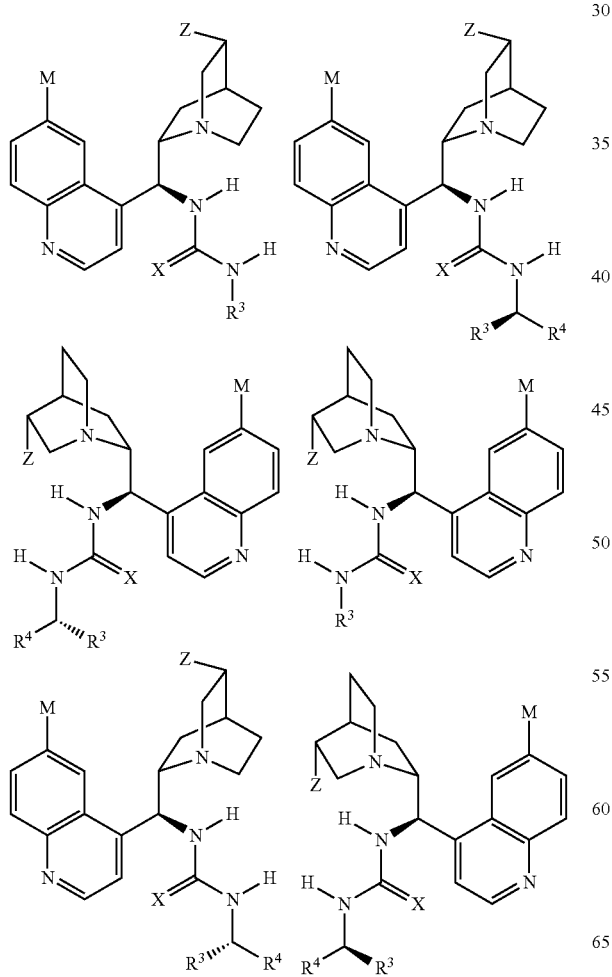

wherein X can be O or S;

Z can be a single or double bond;

M can be H, OH, or OMe; and

R$_3$ and R$_4$ can be the same or different and may comprise C$_1$-C$_{15}$ alkyl, or R$_3$ and R$_4$ may together define a C$_3$-C$_{15}$ cycloalkyl alkyl ring or C$_5$-C$_{15}$ aromatic ring.

In one embodiment, the chiral catalyst may be selected from the group consisting of:

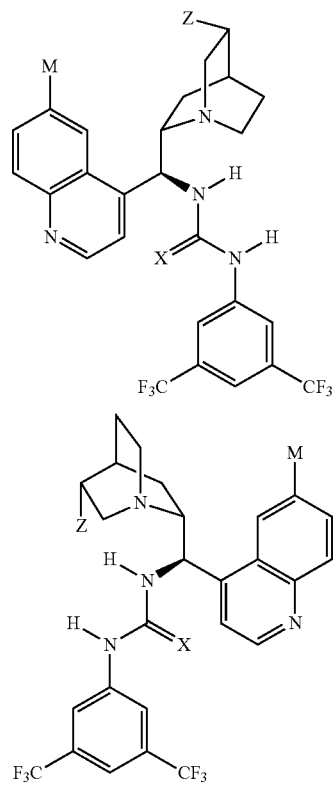

wherein X can be O or S;

Z can be a single or double bond; and

M can be H, OH or OMe.

Desirably, the chiral catalyst is selected from the group comprising:

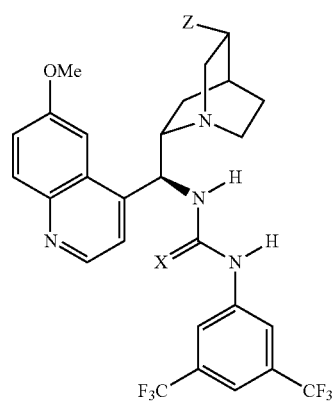

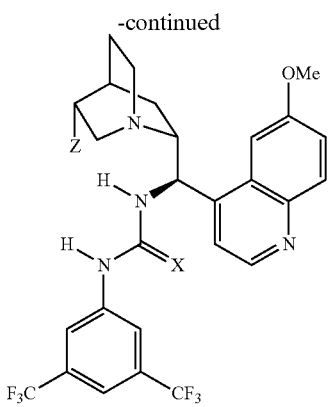

wherein Z can be a double or single bond.

In one embodiment Z is a double bond.

As will be appreciated by a person skilled in the art, the definitions of $C_x$-$C_y$ alkyl, $C_x$-$C_y$ cycloalkyl, $C_x$-$C_y$ aromatic, etc. presented herein embrace substitution of these chains/rings provided such substitutions do not interfere with the thiol mediated thiolysis or alcohol mediated alcoholysis of 3-isobutylglutaric anhydride. Unless otherwise indicated suitable substitutions may comprise halogens, cyano, $CF_3$, and combinations thereof. As used herein, the terms aromatic/aryl encompass heteroaromatic/heteroaryl.

The compounds of the present invention may be found or isolated in the form of esters, salts, hydrates or solvates—all of which are embraced by the present invention.

Where suitable, it will be appreciated that all optional and/or preferred features of one embodiment of the invention may be combined with optional and/or preferred features of another/other embodiment(s) of the invention.

BRIEF DESCRIPTION OF THE DRAWINGS

Additional features and advantages of the present invention are described in, and will be apparent from, the detailed description of the invention and from the drawings in which.

DETAILED DESCRIPTION OF THE INVENTION

It should be readily apparent to one of ordinary skill in the art that the examples disclosed herein below represent generalised examples only, and that other arrangements and methods capable of reproducing the invention are possible, and are embraced by the present invention.

The abbreviations herein under will be adhered to for the remainder of this section:

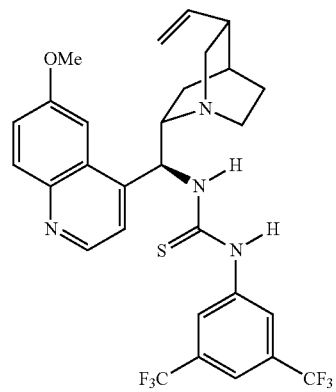

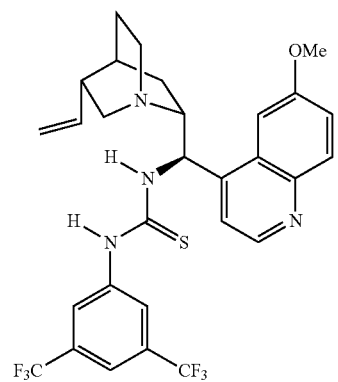

Figure 1:
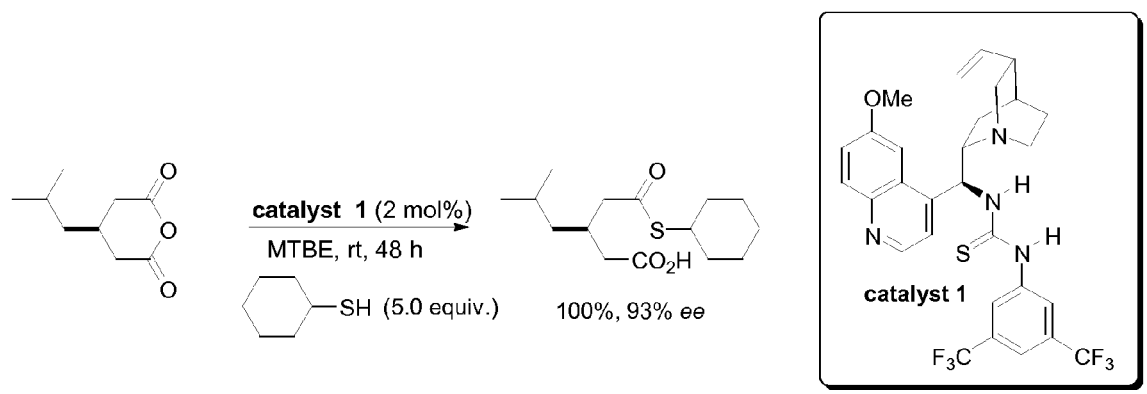
FIG. 1 illustrates catalytic enantioselective thiolysis of 3-isobutylglutaric anhydride using cyclohexane thiol according to the present invention.

A schematic of the catalytic enantioselective thiolysis of 3-isobutylglutaric anhydride using cyclohexane thiol to afford (R)-3-cyclohexylsulfanylcarbonylmethyl-5-methyl-hexanoic acid is provided in FIG. 1. Thiolysis of 3-isobutyl-glutaric anhydride in methyltertbutylether (MTBE), at room temperature (rt) in the presence of catalytic quantities of C1 affords 3-cyclohexylsulfanylcarbonylmethyl-5-methyl-hexanoic acid in quantitative yield with the (R) enantiomer obtained in 93% ee.

Figure 2:
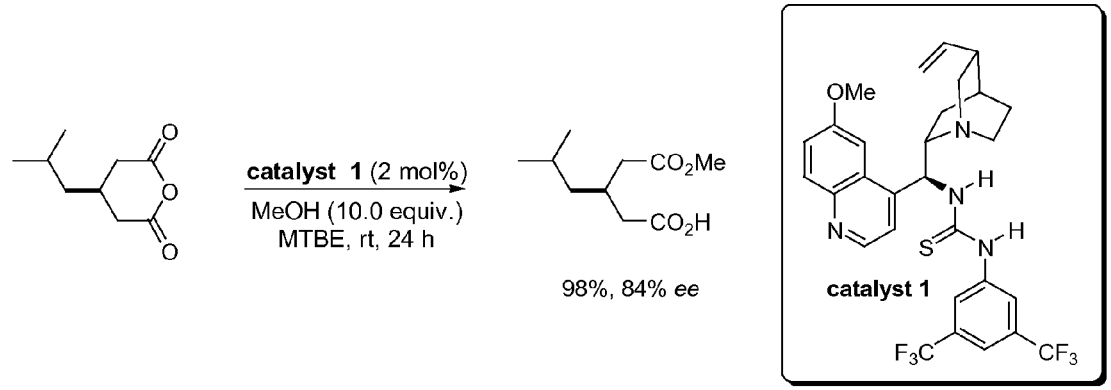
FIG. 2 illustrates catalytic enantioselective alcoholysis of 3-isobutylglutaric anhydride using methanol according to the present invention.

Similarly, FIG. 2 depicts catalytic enantioselective alcoholysis of 3-isobutylglutaric anhydride using methanol. Alcoholysis of 3-isobutylglutaric anhydride in methyltertbutylether (MTBE), at room temperature, in the presence of catalytic quantities epimeric quinine thiourea C1 affords 3-isobutyl-pentanedioic acid monomethyl ester in near quantitative yield with the (R) enantiomer obtained in 84% ee.

Both the alcoholysis and thiolysis reactions proceed highly efficiently and with excellent enantioselectivity with extremely low catalyst loadings of 2 mol % relative to 3-isobutylglutaric anhydride.

Figure 3:
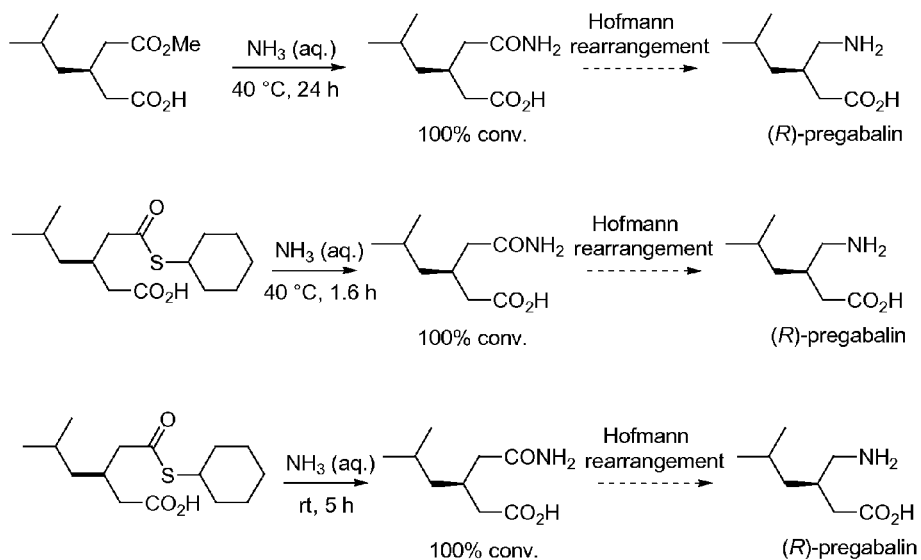
FIG. 3 illustrates aminolysis of ester and thioester intermediates according to the present invention.

Aminolysis of (R)-3-isobutyl-pentanedioic acid monomethyl ester and (R)-3-cyclohexylsulfanylcarbonylmethyl-5-methyl-hexanoic in aqueous ammonia is provided in FIG. 3. Aminolysis of the thioester derivative occurs more rapidly (1.6 hours versus 40 hours) and under milder conditions that the corresponding ester intermediate. In fact, quantitative aminolysis of the thioester intermediate could be effected at room temperature over a period of 5 hours.

Figure 4:
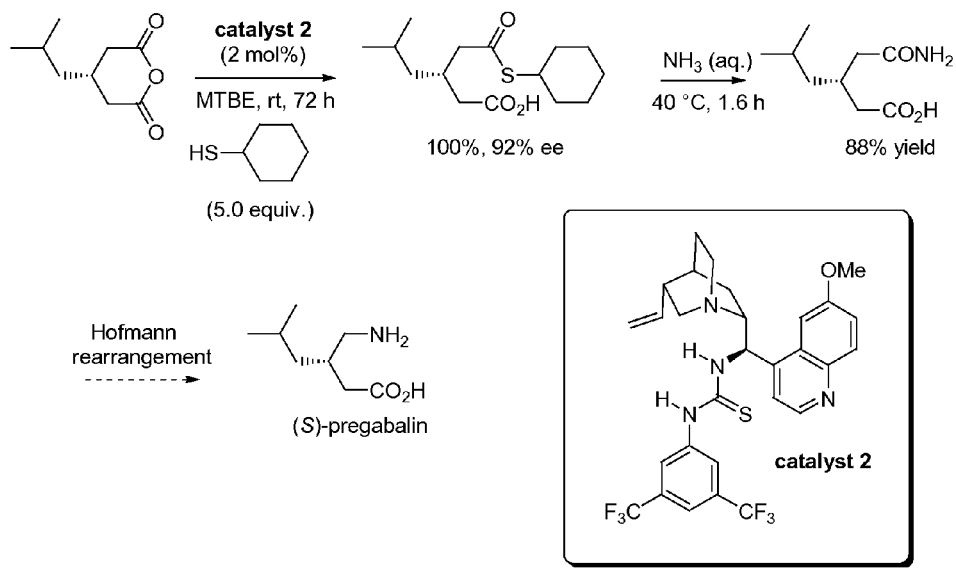
FIG. 4 illustrates a synthesis of (S)-pregabalin according to the present invention.

FIG. 4 demonstrates a room temperature enantioselective synthesis of (S)-pregabalin in the presence of catalytic quantities of epimeric quinidine thiourea C2. Thiolysis of 3-isobutylglutaric anhydride with cyclohexane thiol in methyltertbutylether (MTBE), at room temperature (rt) in the presence of catalytic quantities of C2 affords (S)-3-cyclohexylsulfanylcarbonylmethyl-5-methyl-hexanoic acid in quantitative yield and in 92% ee (the ee increased to 94% when the reaction was carried out at 0° C.). Aminolysis of resulting thioester intermediate at 40° C. over 1.6 h afforded (S)-3-Carbamoylmethyl-5-methyl-hexanoic acid in 88% yield. This primary amide intermediate was subjected to a Hofmann rearrangement to afford (S)-pregabalin.

EXPERIMENTAL PROCEDURES

Desymmetrisation of 3-Isobutylglutaric Anhydride by Thiolysis Using Catalyst C2 at Ambient Temperature A 60 mL reaction vial, charged with 3-isobutylglutaric anhydride (102.1 mg, 0.60 mmol) and C2 (7.1 mg, 0.012 mmol), was fitted with a septum and flushed with argon. MTBE (40 mL) was added followed by cyclohexyl mercaptan (368 μL, 3.0 mmol) in a dropwise manner via syringe. After 72 h stirring at room temperature, volatiles were removed under reduced pressure and the desired product (VI) obtained, after purification by flash chromatography, in 100% yield (164.0 mg) as a colourless oil. $[\alpha]_D^{20}=-5.9$ (c 1.64, acetone).

$\delta_H$(400 MHz, CDCl$_3$): 0.92 (app. d, J 6.5, 6H), 1.18-1.34 (m, 3H), 1.36-1.50 (m, 4H), 1.56-1.78 (m, 4H), 1.88-1.98 (m, 2H), 2.34-2.52 (m, 3H), 2.56-2.64 (m, 2H), 3.48-3.59 (m, 1H). $\delta_C$(100 MHz, CDCl$_3$): 22.0, 22.1, 24.7, 25.0, 25.5, 30.0, 32.5, 32.6, 37.6, 41.9, 42.7, 47.5, 176.7, 198.2. HRMS (ESI): Found 285.1522 (M–H$^+$) C$_{15}$H$_{25}$O$_3$S requires 285.1524.

92% ee as determined by CSP-HPLC analysis of the corresponding o-nitrophenoxy ester prepared as below.

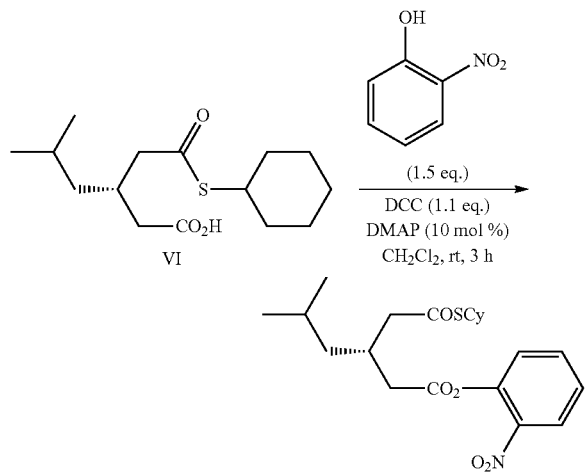

A 5 mL reaction vial containing a stirring bar was charged with the appropriate hemi(thio)ester (0.10 mmol), 2-nitrophenol (20.9 mg, 0.15 mmol) and DMAP (1.2 mg). The vial was flushed with argon and the resulting mixture was dissolved in dry CH$_2$Cl$_2$ (0.5 mL). A solution of DCC (23.0 mg, 0.11 mmol) in dry CH$_2$Cl$_2$ (0.5 mL) was then added and the reaction mixture was stirred for 3 h at room temperature. After filtration of the resulting white precipitate, the filtrate was concentrated in vacuo and the residue was purified by chromatography on silica gel to afford the desired compound in quantitative yield.

Chiralpak OD-H (4.6 mm×25 cm), hexane/IPA:90/10, 0.2 mL min$^{-1}$, RT, UV detection at 220 nm, retention times: 30.3 min (minor enantiomer) and 32.0 (major enantiomer).

Desymmetrisation of 3-Isobutylglutaric Anhydride by Thiolysis Using Catalyst C2 at Low Temperature Procedure A A 40 mL reaction vial containing a stirring bar was charged with 3-isobutylglutaric anhydride (51.1 mg, 0.30 mmol) and C2 (3.6 mg, 0.006 mmol).

The reaction vial was fitted with a septum and flushed with argon. MTBE (20 mL) was added and the solution was cooled to 0° C. Cyclohexyl mercaptan (184 μL, 1.50 mmol) was added dropwise via syringe. After 72 h conversion to the desired product was determined to be 93% by H-NMR analysis. The reaction was then quenched by addition of HCl (1N, 10 mL). The resulting biphasic mixture was transferred to a separating funnel and the aqueous phase was extracted with EtOAc (3×15 mL). The organic phases were combined, dried over MgSO$_4$, and concentrated in vacuo to provide the desired hemithioester, after purification by flash-chromatography, in 94% ee.

Procedure B

A 40 mL reaction vial containing a stirring bar was charged with 3-isobutylglutaric anhydride (51.1 mg, 0.30 mmol) and C2 (5.4 mg, 0.009 mmol). The reaction vial was fitted with a septum and flushed with argon. MTBE (20 mL) was added and the solution was cooled to 0° C. Cyclohexyl mercaptan (184 μL, 1.50 mmol) was added dropwise via syringe. After 48 h, conversion into the desired product was determined to be 94% by H-NMR analysis. The reaction was then quenched by addition of HCl (1N, 10 mL). The resulting biphasic mixture was transferred to a separating funnel and the aqueous phase was extracted with EtOAc (3×15 mL). The organic phases were combined, dried over MgSO$_4$ and concentrated in vacuo to provide the desired hemithioester, after purification by flash-chromatography, in 94% ee.

Amidation of Hemithioester (VI) with Aqueous Ammonia at 40° C.

A 25 mL round bottom flask, charged with (+3-cyclohexylsulfanylcarbonylmethyl-5-methyl-hexanoic acid (VI) (164.0 mg, 0.60 mmol, 92% ee) and aqueous NH$_3$ (35%, 6 mL), was equipped with a reflux condenser and heated to 40° C. After 1.6 h stirring, the solution was concentrated in vacuo, water (10 mL) was added and the aqueous phase was washed twice with EtOAc (5 mL). The combined organic extracts were further washed with water (5 mL) and the combined aqueous layers were acidified by addition of HCl (1N) and extracted with EtOAc (5×15 mL). The combined organic phases were then dried over magnesium sulphate and the solvent was removed under reduced pressure to afford the desired compound as a white solid (99.0 mg, 88% yield). M.p. 105-106° C.

$\delta_H$ (400 MHz, DMSO-d$_6$): 0.81 (app d, J 6.6, 6H), 1.09 (app t, J 6.6, 2H), 1.51-1.66 (m, 1H), 1.91-2.22 (m, 5H), 6.74 (s, 1H), 7.27 (s, 1H), 12.0 (br s, 1H). $\delta_C$ (100 MHz, DMSO-d$_6$): 23.1, 23.2, 25.0, 30.1, 39.2, 40.2, 43.6, 173.8, 174.3. HRMS (ESI): Found 210.1114 (M+Na$^+$) C$_9$H$_{17}$NO$_3$Na requires 210.1106.

Maintenance of Stereochemical Integrity During Aminolysis Procedure:

To confirm that no racemisation occurred during the aminolysis step, the enantioenriched product was transformed into the corresponding o-nitrophenoxy ester and analyzed by CSP-HPLC.

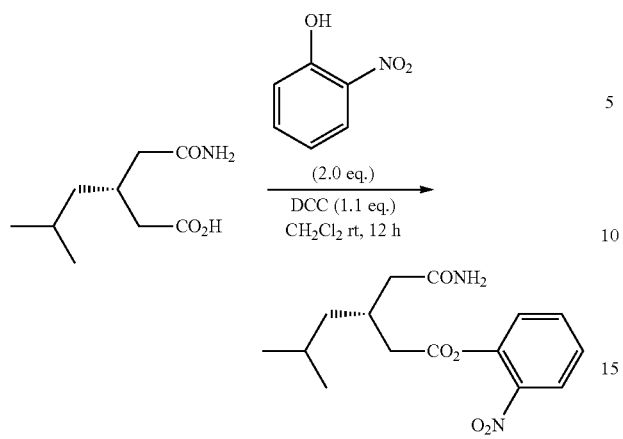

A 5 mL reaction vial containing a stirring bar was charged with (+)-3-carbamoylmethyl-5-methyl-hexanoic acid (0.10 mmol) and 2-nitrophenol (27.8 mg, 0.20 mmol). The vial was flushed with argon and dry $CH_2Cl_2$ (0.5 mL) was added. A solution of DCC (23.0 mg, 0.11 mmol) in dry $CH_2Cl_2$ (0.5 mL) was then added via syringe and the reaction mixture was stirred for 12 h at room temperature. After filtration of the resulting white precipitate, the filtrate was concentrated in vacuo and the residue was purified by chromatography on silica gel to afford the desired compound in quantitative yield. 92% ee as determined by CSP-HPLC analysis. Chiralpak AD-H (4.6 mm×25 cm), hexane/IPA:90/10, 1.0 mL $min^{-1}$, RT, UV detection at 220 nm, retention times: 13.5 min (major enantiomer) and 14.5 (minor enantiomer).

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A compound of the general formula (I), or a salt, or ester thereof,

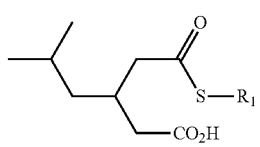
(I)

wherein $R_1$ is selected form the group consisting of $C_1$-$C_{15}$ alkyl, $C_3$-$C_{15}$ cycloalkyl, $C_5$-$C_{15}$ aromatic and combinations thereof.

2. A compound according to claim 1 of the general formula (II), or a salt, or ester thereof,

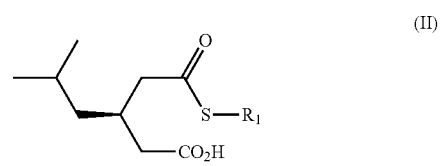
(II)

wherein $R_1$ is selected form the group consisting of $C_1$-$C_{15}$ alkyl, $C_3$-$C_{15}$ cycloalkyl, $C_5$-$C_{15}$ aromatic and combinations thereof.

3. A compound according to claim 1 of the general formula (III), or a salt, or ester thereof,

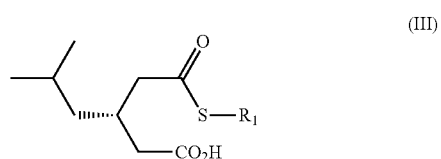
(III)

wherein $R_1$ is selected form the group consisting of $C_1$-$C_{15}$ alkyl, $C_3$-$C_{15}$ cycloalkyl, $C_5$-$C_{15}$ aromatic and combinations thereof.

4. A process for the preparation of a compound of the formula (I),

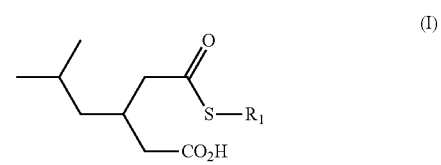
(I)

wherein $R_1$ is selected form the group consisting of $C_1$-$C_{15}$ alkyl, $C_3$-$C_{15}$ cycloalkyl, $C_5$-$C_{15}$ aromatic and combinations thereof.

5. A process according to claim 4, wherein the compound is:

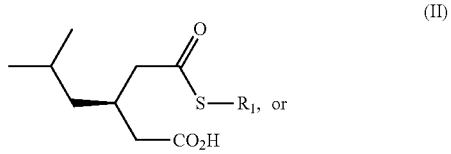
(II)

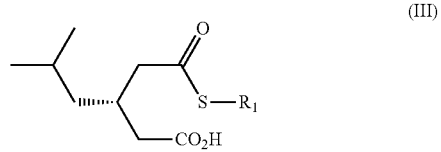
(III)

or a salt, or ester thereof and wherein the process is enantioselective and comprises enantioselective thiolysis of 3-isobutylglutaric anhydride to afford a compound having a thioester functional group.

6. A process according to claim 5 wherein the enantioselective thiolysis step comprises ring opening 3-isobutylglutaric anhydride using a chiral thiol.

7. A process according to claim 5 wherein the enantioselective thiolysis step comprises ring opening 3-isobutylglutaric anhydride using an achiral thiol and a chiral catalyst.

8. A process according to claim 7 wherein the chiral catalyst comprises:
i) a Lewis acid functional group to enhance the electrophilicity of 3-isobutylglutaric anhydride; and
ii) a Lewis base functional group to enhance the nucleophilicity of the achiral thiol.
9. A process according to claim 8 wherein the catalyst is selected from the group consisting of
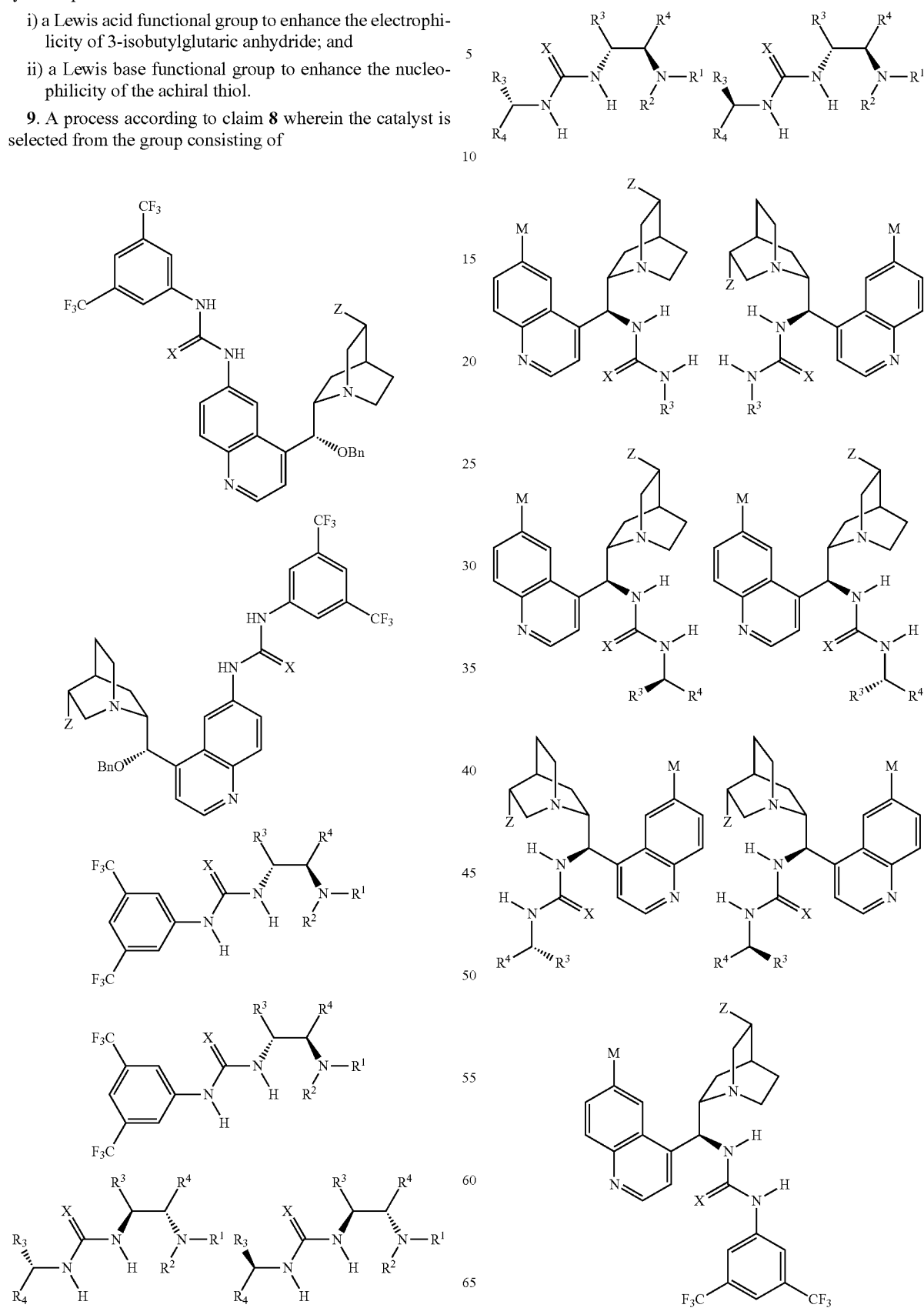

-continued

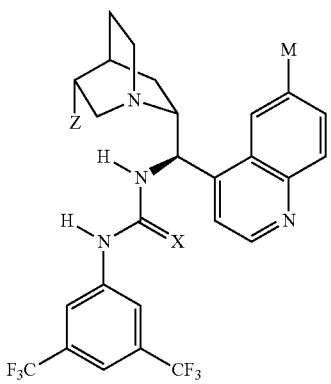

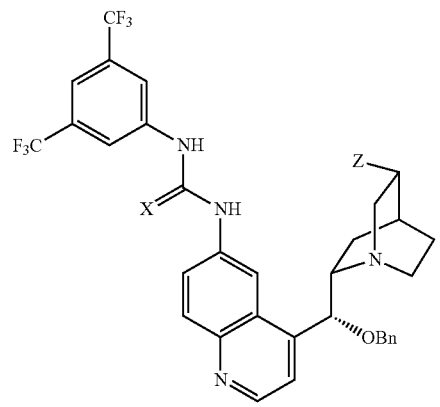

wherein X is O or S;
- Z is a $C_1$ to $C_5$ carbon chain optionally having at least one C—C unsaturated bond;
- M is H, OH, or OMe;
- $R_1$ and $R_2$ may be the same or different and are $C_1$-$C_{15}$ alkyl, or $R_1$ and $R_2$ taken together with the N to which they are attached define a $C_3$-$C_{15}$ heterocycloalkyl ring; and
- $R_3$ and $R_4$ may be the same or different and are $C_1$-$C_{15}$ alkyl, or $R_3$ and $R_4$ taken together define a $C_3$-$C_{15}$ cycloalkyl ring or $C_5$-$C_{15}$ aromatic ring.

10. A process for the enantioselective preparation of a compound of the general formula (IV) or (V), or a salt thereof, comprising:

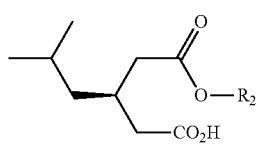 (IV)

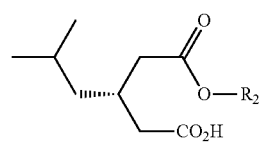 (V)

enantioselective alcoholysis of 3-isobutylglutaric anhydride to afford a compound having an ester functional group,
wherein enantioselective alcoholysis of 3-isobutylglutaric anhydride comprises ring opening 3-isobutylglutaric anhydride using an achiral alcohol and a chiral catalyst selected from the group consisting of:

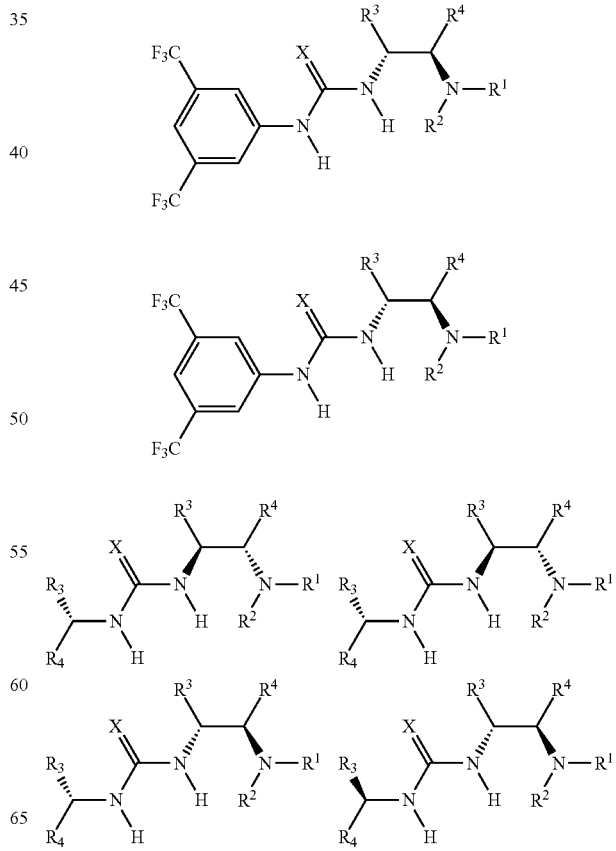

-continued

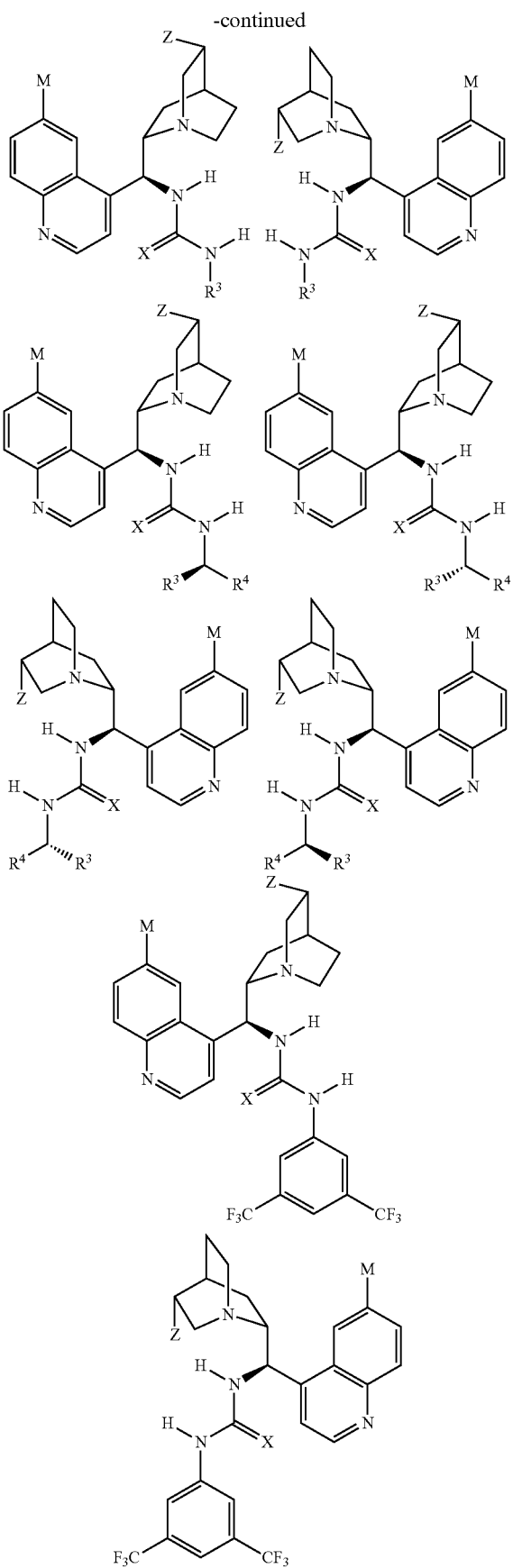

wherein X is O or S;
Z is a $C_1$ to $C_5$ carbon chain optionally having at least one C—C unsaturated bond;
M is H, OH, or OMe;
$R_1$ and $R_2$ may be the same or different and are $C_1$-$C_{15}$ alkyl, or $R_1$ and $R_2$ taken together with the N to which they are attached define a $C_3$-$C_{15}$ heterocycloalkyl ring; and
$R_3$ and $R_4$ may be are the same or different and are $C_1$-$C_{15}$ alkyl, or $R_3$ and $R_4$ taken together define a $C_3$-$C_{15}$ cycloalkyl ring or $C_5$-$C_{15}$ aromatic ring.

11. A process for the preparation of 3-(aminomethyl)-5-methyl-hexanoic acid comprising:
   i) thiolysis of 3-isobutylglutaric anhydride according to claim 4 to afford an intermediate having a thioester functional group; and
   ii) converting the thioester functional group into an amine.

12. A process for the enantioselective preparation of 3-(aminomethyl)-5-methyl-hexanoic acid comprising:
   i) enantioselective thiolysis of 3-isobutylglutaric anhydride according to claim 5 to afford an intermediate having a thioester functional group;
   and
   ii) converting the thioester functional group into an amine.

13. A process according to claim 12 wherein the step of converting the thioester functional group into an amine comprises:
   i) aminolysis of the thioester functional group to yield an amide; and
   ii) subjecting the amide product of step i) to a Hofmann rearrangement.

14. A process according to claim 11, wherein the step of converting the thioester functional group into an amine comprises:
   i) aminolysis of the thioester functional group to yield an amide; and
   ii) subjecting the amide product of step i) to a Hofmann rearrangement.

15. A process for the enantioselective preparation of 3-(aminomethyl)-5-methyl-hexanoic acid comprising:
   i) enantioselective alcoholysis of 3-isobutylglutaric anhydride according to claim 10 to afford a chiral intermediate having an ester functional group; and
   ii) converting the ester functional group into an amine.

16. A process according to claim 15 wherein the step of converting the ester functional group into an amine comprises:
   i) aminolysis of the ester functional group to yield an amide; and
   ii) subjecting the amide product of step i) to a Hofmann rearrangement.

* * * * *